United States Patent
Savkovic et al.

(10) Patent No.: US 9,801,977 B2
(45) Date of Patent: Oct. 31, 2017

(54) METHOD FOR DERIVING MELANOCYTES FROM THE HAIR FOLLICLE OUTER ROOT SHEATH AND PREPARATION FOR GRAFTING

(71) Applicants: Vuk Savkovic, Leipzig (DE); Christina Dieckmann, Leipzig (DE); Jan-Christoph Simon, Leipzig (DE); Michaela Schulz-Siegmund, Leipzig (DE); Michael Hacker, Leipzig (DE)

(72) Inventors: Vuk Savkovic, Leipzig (DE); Christina Dieckmann, Leipzig (DE); Jan-Christoph Simon, Leipzig (DE); Michaela Schulz-Siegmund, Leipzig (DE); Michael Hacker, Leipzig (DE)

(73) Assignee: UNIVERSITÄT LEIPZIG, Leipzig (DE)

( * ) Notice: Subject to any disclaimer, the term of this patent is extended or adjusted under 35 U.S.C. 154(b) by 61 days.

(21) Appl. No.: 14/354,545

(22) PCT Filed: Oct. 29, 2012

(86) PCT No.: PCT/EP2012/071418
§ 371 (c)(1),
(2) Date: Apr. 25, 2014

(87) PCT Pub. No.: WO2013/060899
PCT Pub. Date: May 2, 2013

(65) Prior Publication Data
US 2015/0086513 A1    Mar. 26, 2015

(30) Foreign Application Priority Data

Oct. 27, 2011 (EP) .................................... 11186944
Aug. 30, 2012 (EP) .................................... 12182385

(51) Int. Cl.
| | | |
|---|---|---|
| C12N 5/071 | (2010.01) | |
| A61K 35/36 | (2015.01) | |
| A61L 27/38 | (2006.01) | |
| A61L 27/60 | (2006.01) | |

(52) U.S. Cl.
CPC ....... *A61L 27/3834* (2013.01); *A61L 27/3895* (2013.01); *A61L 27/60* (2013.01); *C12N 5/0626* (2013.01); *C12N 2500/02* (2013.01); *C12N 2500/38* (2013.01); *C12N 2501/33* (2013.01); *C12N 2501/81* (2013.01); *C12N 2506/03* (2013.01); *C12N 2533/40* (2013.01)

(58) Field of Classification Search
CPC ...................... C12N 5/0626; C12N 2506/1376
See application file for complete search history.

(56) References Cited

U.S. PATENT DOCUMENTS

| | | | |
|---|---|---|---|
| 2005/0170330 A1* | 8/2005 | Amoh ................ | G01N 33/5073 435/4 |
| 2010/0273231 A1* | 10/2010 | Andreadis ............... | A61F 2/062 435/177 |
| 2011/0305671 A1* | 12/2011 | Armani ................ | A61K 9/0019 424/93.3 |

OTHER PUBLICATIONS

Zhu et al "Isolation and Culture of Amelanotic Melanocytes from Human Hair Follicles" Pigment Cell Res, 2004, vol. 17, pp. 668-673.*
Bretscher MS. On the shape of migrating cells—a 'front-to-back' model. J. Cell. Sci. 2008; 121:2625-2628 PubMed.
Horwitz R, Webb D. Cell migration. Curr. Biol. 2003; 13:R756-9 PubMed.
Mishima Y, Widlan S. Embryonic development of melanocytes in human hair and epidermis. Their cellular differentiation and melanogenic activity. J Invest Dermatol. Mar. 1966; 46(3):263-77.
Petrie RJ, Doyle AD, Yamada KM. Random versus directionally persistent cell migration. Nat. Rev. Mol. Cell Biol. 2009; 10:538-49 PubMed.
R.G. Staricco. Preliminary and short report: Amelanotic melanocytes in the outer sheath of the human hair follicle. J. Invest. Dermat., 33 (1959), pp. 295-297.
Raposo G, Marks MS (2007). "Melanosomes—dark organelles enlighten endosomal membrane transport." Nat Rev Mol Cell Biol. 8 (10): 786-797.
Staricco, Renato G. Amelanotic melanocytes in the outer sheath of the human hair follicle and their role in the repigmentation of regenerated epidermis. The Pigment Cell Molecular, Biological, and Clinical Aspects: Part I, vol. 100, 239-255, Feb. 1963.
Tatsuya Horikawa, David A. Norris, Thomas W. Johnson, Tamara Zekman, Nancy Dunscomb, Scott D. Bennion, Ronald L. Jackson, Joseph G. Morelli. DOPA-Negative Melanocytes in the Outer Root Sheath of Human Hair Follicles Express Premelanosomal Antigens But Not a Melanosomal Antigen or the Melanosome-Associated Glycoproteins Tyrosinase, TRP-1, and TRP-2. Journal of Investigative Dermatology, vol. 106, Issue 1, 1996, pp. 28-35.
Lunec et al., 1990 Alpha-melanocyte-stimulating hormone immunoreactivity in melanoma cells. Pathobiology 58:193-197.
Commo et al., Human Hair Greying Is Linked to a Specific Depletion of Hair Follicle Malanocytes Affecting Both the Bulb and the Outer Root Sheath; British Journal of Dermatology 2004; 150: 435-443.
Cui et al., Role of Hair Follicles in the Repigmentation of Vitiligo; The Journal of Investigative Dermatolgy vol. 97, pp. 410-416, 1991.
Kirkpatrick et al., Biochim Biophys Acta,. Jul. 30, 1985;846(1):120-6.

(Continued)

*Primary Examiner* — Allison Fox
(74) *Attorney, Agent, or Firm* — Faegre Baker Daniels LLP

(57) ABSTRACT

The present invention relates to the field of biology and medicine, and more specifically, to the field of stem-cell biology, involving producing or generating melanocytes from stem-cells and precursors derived from human hair root. Additionally, the present invention relates to the materials and method for producing autografts, homografts or allografts comprising melanocytes in general, as well as the materials and methods for producing autografts, homografts and allografts comprising melanocytes for the treatment of diseases related to depigmentation of the skin and for the treatment of scars.

30 Claims, 17 Drawing Sheets

(56) References Cited

OTHER PUBLICATIONS

Ma et al., A Modified Method for Purifying Amelanotic Melanocytes From Human Hair Follicles; Journal of Dermatology vol. 33, pp. 239-248, 2006.
Masson-Pevet et al., Journal of Molecular and Cellular Cardiology, vol. 8, Issue 10, Oct. 1976, pp. 747-748, IN1-IN11, 749-757.
Nishimura et al., Dominant Role of the Niche in Melanocyte Stem-Cell Fate Determination; Nature, vol. 415, Apr. 25, 2002 pp. 854-860.
Pillai et al., Cryobiology, vol. 47, Issue 3, Dec. 2003, pp. 242-246.
Tobin et al., The Fate of Hair Follicle Melanocytes During the Hair Growth Cycle; Journal of Investigative Dermatology Symposium Proceedings 4:323-332, 1999.
Wakamatsu et al., (1997) Characterisation of ACTH peptides in human skin and their activation of the melanocortin-1 receptor. Pigment Cell Res 10:288-297.
International Search Report and Written Opinion issued by the European Searching Authority for 071418 dated Mar. 24, 2013, 19 Pages.
Dieckmann Christina et al: "Human melanocytes can be isolated, propagated and expanded from plucked anagen hair follicles.", Experimental Dermatology Jun. 2010 LNKD—Pubmed:20374294, vol. 19, No. 6, Jun. 2010 (Jun. 2010)' pp. 543-545, XP055022886, ISSN: 1600-0625.
Szabad Gabor el al: "Human adult epidermal melanocytes cultured without chemical mitogens express the EGF receptor and respond to EGF.", Archives of Dermatological Research Jul. 2007 LNKD—Pubmed:17334773, vol. 299, No. 4, Jul. 2007 (Jul. 2007), pp. 191-200, XP019516655, ISSN: 0340-3696.
Kauser Sobia et al: 'A fully functional proopiomelanocortin;melanocortin-1 receptor system regulates the differentiation of human scalp hair follicle melanocytes.', Endocrinology Feb. 2005 LNKD•Pubmed:15498881, vol. 146, No. 2, Feb. 2005 (Feb. 2005), pp. 532-543, XP009055354, ISSN: 0013-7227.
Liu F et al: 'Using human hair follicle-derived keratinocytes and melanocytes for constructing pigmented tissue-engineered skin'. Skin Research and Technology 2011 Blackwell Publishing LTD GBR, vol. 17, No. 3, Aug. 2011 (Aug. 2011), pp. 373-379, XP002670158, ISSN: 0909-752X.
Swope Viki B et al: 'Regulation of cutaneous pigmentation by titration of human melanocytes 1n cultured skin substitutes grafted to athymic mice.', Wound Repair and Regeneration Official Publication of the Wound Healing Society [and] The European Tissue Repair Society Nov.-Dec. 2002, vol. 10, No. 6, Nov. 2002 (Nov. 2002), pp. 378-386, XP002487800, ISSN: 1067-1927.
Hartmann A et al: Repigmentation of skin anc hair in stable vitiligo by transplantation of autologous melanocytes 1n fibrin suspension., Journal of the European Academy of Dermatology and Venereology JEADV May 2008,vol. 22, No. 5, May 2008 (May 2008), pp. 624-626, XP55059636, JSSN: 1468-3083.

* cited by examiner

Figs. 1A-D
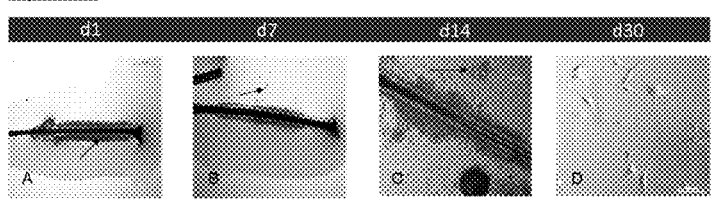

Figs. 2A-1
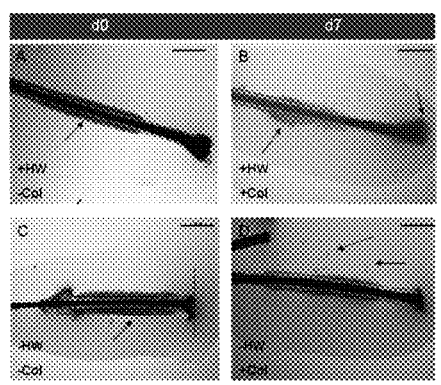
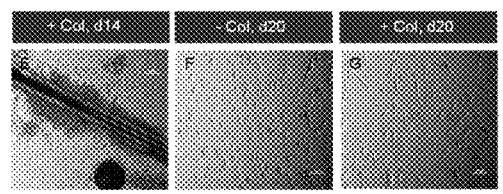
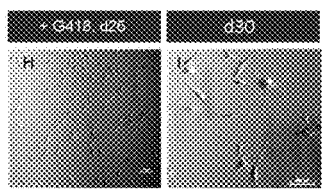

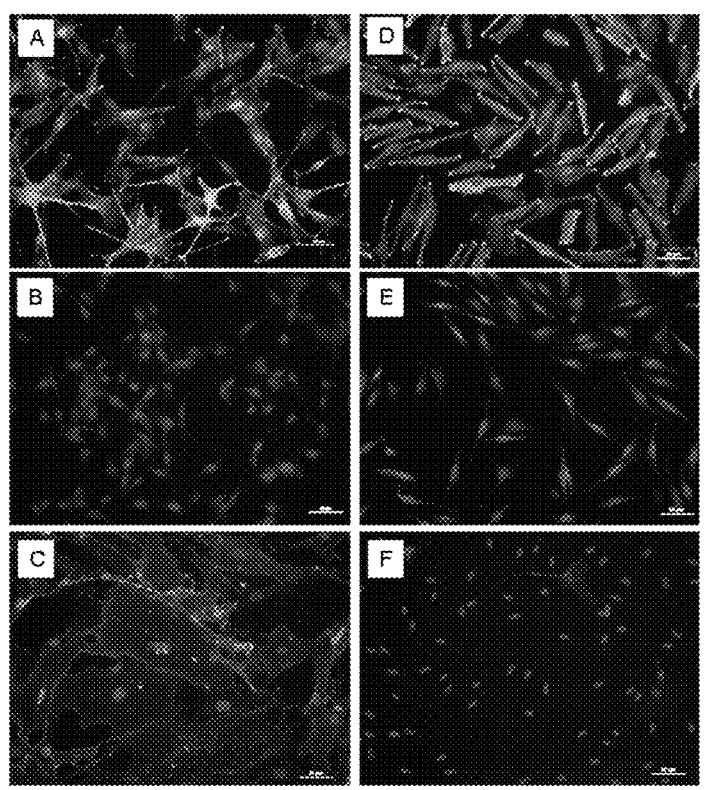
Figs. 3A-F

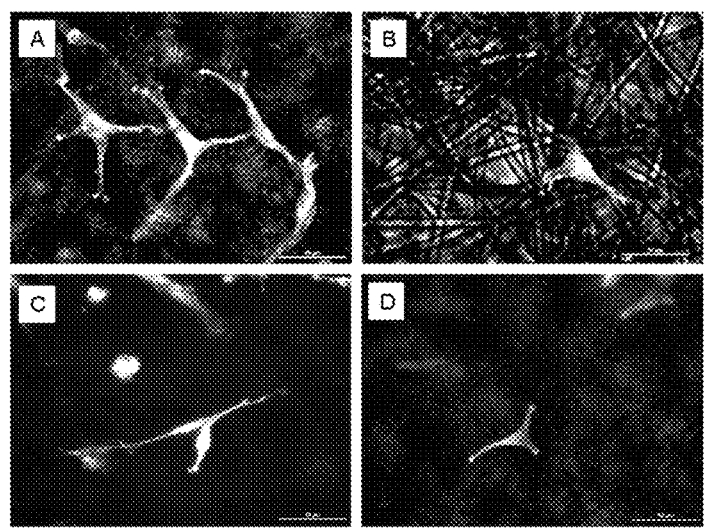
Figs. 9A-D

Figs. 10A-B
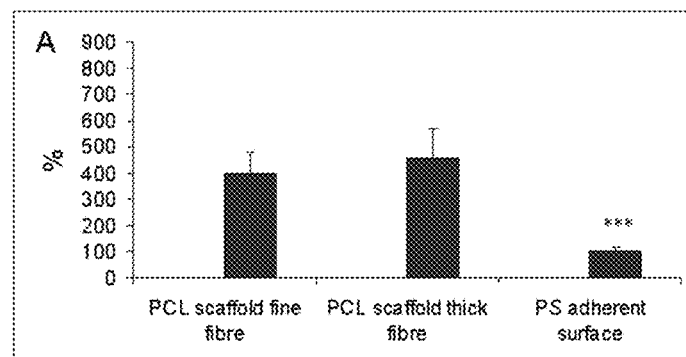
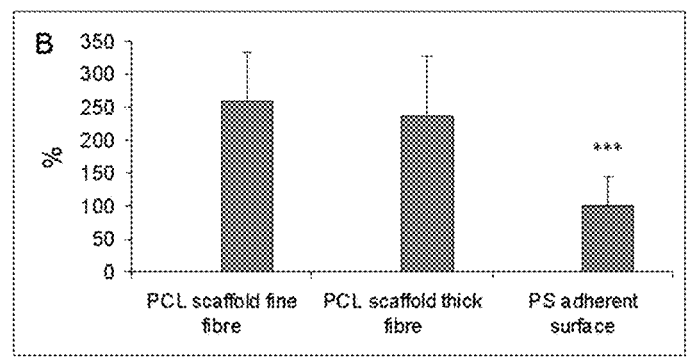

Figs. 10C-D
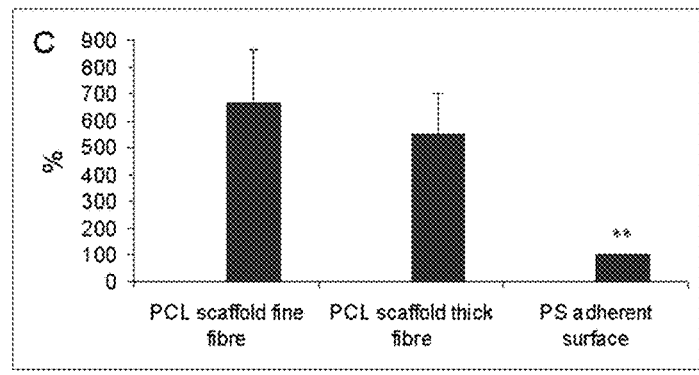
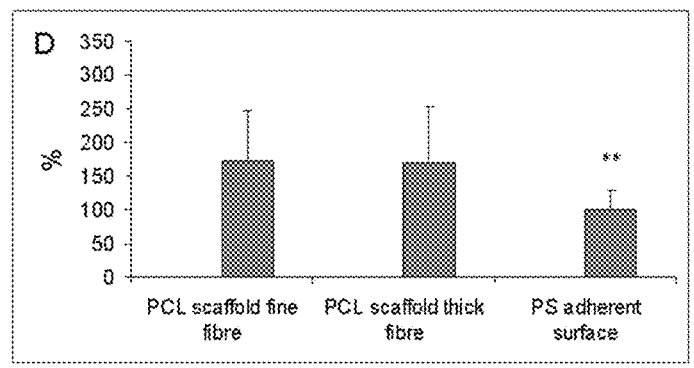

Figs. 11A-B
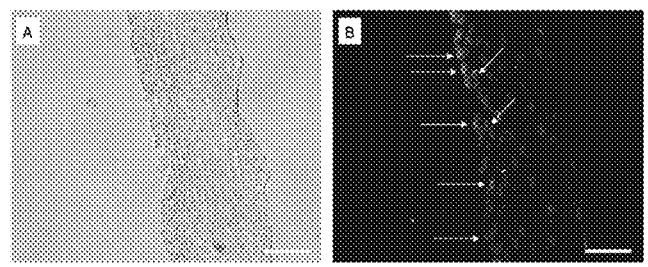

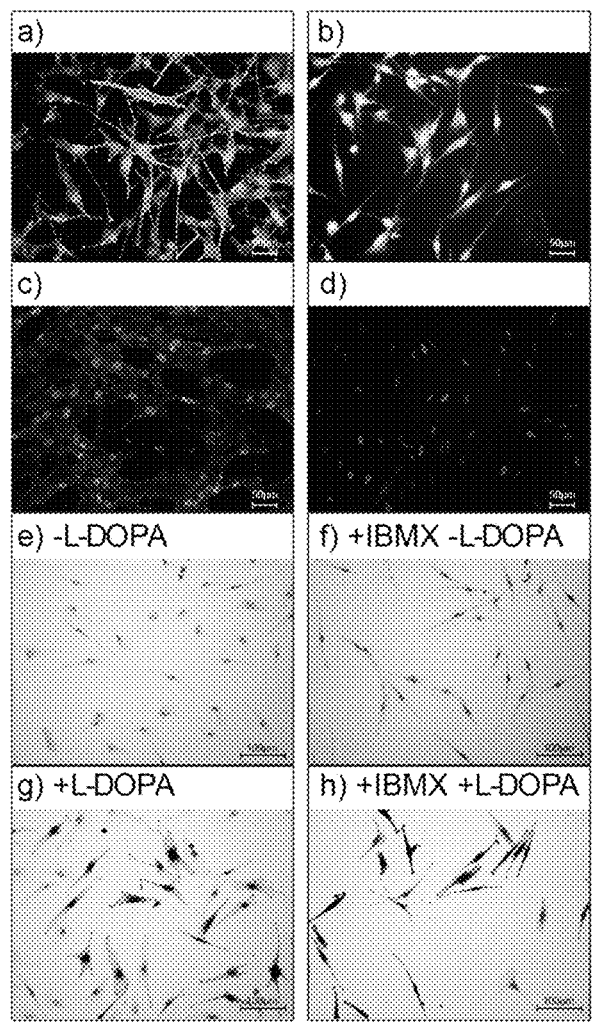

Comparative changes in the Outer Root Sheath surface

Figs. 14A-F

Graphic display of comparative ORS surface changes

Comparative growth in the adherent culture, cell number per hair follicle

US 9,801,977 B2

METHOD FOR DERIVING MELANOCYTES FROM THE HAIR FOLLICLE OUTER ROOT SHEATH AND PREPARATION FOR GRAFTING

CROSS-REFERENCE TO RELATED APPLICATIONS

This application is a U.S. National Stage filing under 35 U.S.C. §371 of International Patent Application No. PCT/EP2012/071418 filed on Oct. 29, 2012 which claims the benefit of EP Application No. 11186944.2 filed Oct. 27, 2011 and EP Application No. 12182385.0 filed Aug. 30, 2012, which are incorporated herein in their entirety for all purposes.

FIELD

The present invention relates to the field of biology and medicine, and more specifically, to the field of stem-cell biology, involving producing or generating melanocytes from stem-cells and precursors derived from human hair root. Additionally, the present invention relates to a method for producing autografts, homografts or allografts comprising melanocytes.

BACKGROUND

Depigmentation is the lightening of the skin, or loss of pigment. Depigmentation of the skin can be caused by a number of local and systemic conditions. The pigment loss can be partial, for instance injury to the skin, or complete, such as in vitiligo, temporary or permanent.

Depigmentation of the skin is a disease landmark in people affected by vitiligo, which produces differing areas of light and dark skin. Next to the cosmetic disadvantages, skin areas with low pigmentation are prone to sun burns or even more adverse effects, which, in the worst case, result in skin cancer. Hence, substantial efforts are currently undertaken to provide an easy and reliable method for protecting these depigmented areas by providing pigmentation. One approach is to apply melanocytes on the depigmented skin areas. Melanocytes are melanin-producing cells, inter alia, located in the bottom layer (the stratum basale) of the skin epidermis. Melanin is the pigment that primarily determines the color of the skin and enables its primary protection from sun radiation.

Existing medical treatments for vitiligo are partially helpful and are either palliative or invasive. Therefore, a high health interest and market potential exist for a causative, autologous, non-invasive treatment.

The developmental potential of the hair follicle outer root sheath (ORS), which contains pluripotent adult stem cells, transiently amplifying cells, precursors and differentiated cells, is known. These cells are capable of giving rise to melanocytes (among other cell types). Several methodological upgrades have been addressing duration, yield and culture purity since the first long-term cultivation of human hair follicle melanocytes (HM) in 1995 (Tobin D J, Colen S R, Bystryn J C. J Invest Dermatol 1995: 104: 86-89).

However, there is a need for methods to isolate and differentiate melanocyte-yielding cells in order to retrieve pure melanocytes for further processing and application on the skin. Furthermore, there is a need to provide a method to increase the number of yielded melanocytes after a short period of culture. The inventors now provide means and methods as disclosed herein below solving that problem.

The inventors furthermore, found that such melanocytes are very suitable for treatment of depigmentation and are able to show unexpectedly high melanin production and a high enzymatic efficacy in three-dimensional structures.

There are methods known how to obtain and cultivate melanocytes. One approach is the differentiation and cultivation of melanocytes from stem cells from hair follicles (WO-A2 2009/049734). For such purpose, epilated hairs are treated enzymatically to release the stem cells from the hair follicle. After differentiation and cultivation, application to the affected areas was suggested. However, the inventors found that by the method disclosed in WO-A2 2009/049734 also cell types that are surplus to requirements of the treatment, such as fibroblasts and keratinocytes, are cultivated which show adverse effects on the efficacy of the treatment. With known methods the superfluous cell types are also being cultivated, which leads to a loss of efficacy of the depigmentation therapy or makes it more complicated at its best. Hence, there is a need for improved methods to generate and obtain melanocytes. Moreover, there is a need to provide such cells with high purity.

Dieckmann et al. (2010); Experimental Dermatology; 19(6):543-545 discloses a non-invasive method for obtaining these adult stem cells from outer root sheath (ORS) of a plucked hair follicle. However, Dieckmann (loc. cit.) does not disclose (1) that the bulb of an epilated human hair is removed and the remaining part of the epilated hair be used; and (2) that the epilated hair are treated with collagenase. In addition, the cultivation in accordance with the herein provided method can comprise a step of selecting and/or isolating melanocytes comprising Geneticin treatment. Such a step is not disclosed in Dieckmann (loc. cit.).

As shown in Example 2, the method of the present invention allows for a much more pronounced growth and proliferation of melanocytes as compared to the method of Dieckmann (loc. cit.). FIG. 15 shows that the herein provided method provides an exponential increase in the cell number over several passages, whereas the cell number even decreases if the Dieckmann (loc. cit.) method is used. As demonstrated in Example 2, the Dieckmann (loc. cit.) method did not allow for the production of more than 710,000 melanocytes in total whereas the method of the present invention allowed the production of about 80,875,000 melanocytes in total after 6 passages under otherwise comparable conditions. In other words, the present invention provides for a more than 100-fold higher production of melanocytes as compared to the Dieckmann method (loc. cit.). If the corresponding numbers of generated melanocytes per epilated human hair (or likewise per follicle) are calculated, the Dieckmann (loc. cit.) method did not allow for the production of more than about 7,000 (more exactly 7,717 melanocytes) per epilated human hair (or per follicle), whereas the method of the present invention allowed the production of about 2,700,000 melanocytes per epilated human hair (or per follicle) after 6 passages under otherwise comparable conditions. In other words, the present invention provides for a more than 100-fold higher production of melanocytes as compared to the Dieckmann method (loc. cit.). The method of the present invention can advantageously comprise adherent culture of melanocytes.

A first difference of the herein provided method compared to the Dieckmann (loc. cit.) method is the removal of the bulb of an epilated human hair. It is believed that the bulb contains and carries over major amounts of fibroblasts. By removing the bulb, the epilated hair to be used herein contains/yields less fibroblasts. Thus, there are less fibroblasts at the very start of the herein provided method as compared to Dieckmann (loc. cit.). It is believed that this allows a better growth of melanocytes, because the cell culture is less contaminated with fibroblasts and there is therefore less competition for nutrients and space from the very beginning on.

A second difference of the herein provided method as compared to Dieckmann (loc. cit.) is the incubation of the epilated hair with a collagen degrading agent (like Collagenase). Said incubation can take 10 minutes. The collagen degrading agent loosens the extracellular matrix of the epilated hair. It is believed that said loosening facilitates the leave or migration of stem cells from the extracellular matrix. Thus, the incubation with a collagen degrading agent can separate stem cells from the outer root sheath. As demonstrated in Example 2, FIGS. 13 and 14, the Outer Root Sheath surface/cell number is indeed increased as compared to Dieckmann (loc. cit.), if the method of the present invention is employed. Indeed, the Outer Root Sheath surface/cell number was almost twice as high (factor 1.84) as compared to Dieckmann (loc. cit.).

It is believed that due to that the reduction of fibroblasts and easier/quicker/increased leave of stem cells from the extracellular matrix have the advantageous and surprising effect that the present method allows for a pronounced increase in the growth and development of melanocytes in accordance with the present invention, as demonstrated in Example 2. Dieckmann (loc. cit.) provided no hint to the removal of the bulb or collagenase treatment, let alone any advantages conferred thereby. To the contrary, Dieckmann (loc. cit.) even taught away from enzymatic treatment, because it was potentially unfavourable for the cells.

As explained below, the Geneticin treatment is a further advantageous aspect of the herein provided method. As shown in FIG. 15/16 the use of Geniticin in the method of Dieckmann (loc. cit.) does, in contrast to the herein provided method, not allow for a substantial growth or selection/isolation of melanocytes. The Geneticin treatment in accordance with the present method is advantageous because it targets primarily cells with a rapid metabolism and proliferation, such as fibroblasts and keratinocytes, whereas it hardly affects slowly-dividing melanocytes. Thus, the Geneticin treatment allows for an enrichment of melanocytes in the cell culture and a pronounced increase in melanocyte number. Geneticin treatment in the Dieckmann (loc. cit.) method does not show any such desirable effects. Therefore, it is believed that the cell culture according to Dieckmann (loc. cit.) prior to Geneticin treatment contains, in contrast to the method of the present invention, substantial amounts of fibroblasts and keratinocytes and only a minor amount of melanocytes. Thus, it is believed that the amount of melanocytes after Geneticin treatment of the Dieckmann (loc. cit.) cell culture is not sufficient for efficient selection/isolation and growth of melanocytes.

As explained above, the inventors now developed an improved non-invasive method for obtaining adult stem cells from outer root sheath (ORS) of a plucked hair follicle and differentiation into a pure culture of functional melanocytes. The melanocytes prepared by the method according to the present invention as set out herein can be readily used for treatment of Vitiligo as suspension, liquid or in the form of an aerosol, as single culture or combined with keratinocytes. The melanocytes are further provided in autografts, homografts or allografts together with keratinocytes. The grafts provided are stabilized by biocompatible (scaffold) carriers.

The present invention now allows to obtain melanocytes non-invasively, through differentiation from stem cells from the outer root sheath of epilated human hairs in high quantity and purity, in a small time frame of 4 weeks and less.

SUMMARY

The present invention provides for an enhanced method for generating melanocytes from stem cells and/or melanocyte precursors. Hence, the present invention relates to a method for generating melanocytes from stem cells comprising the steps of:
  (i) removing the bulb of an epilated human hair;
  (iii) (ii) incubating the remaining part of the epilated hair with a collagen degrading agent to separate stem cells from the outer root sheath; and cultivating the separated stem cells in a medium that induces differentiation and stimulates growth of stem cells, melanocyte precursors and melanocytes, wherein the medium comprises one or more growth factor for differentiation into melanotic melanocytes, until only the differentiated melanotic melanocytes remain in the culture.

The inventors unexpectedly discovered that contamination with fibroblasts and other cell types can be greatly reduced if the bulb of the hair is removed. The method according to the present invention produces an increase in the yield of pure melanocytes in a shorter timeframe. The aforementioned materials and methods provide for a way to increase the yield of melanocytes with high purity in a shorter timeframe, especially when compared to, for example, the methods disclosed in Diekmann et al. (2010).

The melanocytes generated by the method according to the present invention are surprisingly well suited for autografts, homografts or allografts. Therefore, the present invention also relates to a method for producing an autograft, homograft or an allograft comprising melanocytes, said method comprising the steps of providing a suspension comprising melanocytes obtainable by a method for generating melanocytes from stem cells according to the present invention; providing a biocompatible carrier; and cultivating the melanocytes on said biocompatible carrier.

The present invention furthermore, relates to an autograft, homograft or allograft obtainable by a method for producing an autograft, homograft or an allograft according to the present invention.

The invention further relates to melanocytes obtainable by a method for generating melanocytes from stem cells and/or melanocyte precursors according to the present invention.

BRIEF DESCRIPTION OF THE DRAWINGS

The following drawings form part of the present specification and are included to further demonstrate certain embodiments. Some embodiments may be better understood by reference to one or more of these drawings alone or in combination with the detailed description of specific embodiments presented.

FIGS. 1A-1D are exemplary images of the cultivation, selection and expansion of ORS cells from the ORS of the hair root into a pure culture of melanocytes within four weeks. A: Mid part of the epilated, preparated temporal hair root set on the Transwell microporous membrane (medium-air-interface) on the first day of cultivation. B: Outgrown ORS with first cells migrating out of ORS. C: Multiplied cells are forming aggregations apart from the ORS. D: Pure culture of ORS melanocytes after four weeks of cultivation.

FIGS. 2A-2I are exemplary images of the improvements of the present invention in developing a pure culture of ORS melanocytes. A: Unprepared, untreated hair. ORS is compact (arrow) B: Unprepared, Collagenase V-treated hair with visible migrated cells outside ORS at mid-part and also outside the proximal (bulb) part (arrows). C: Prepared hair with the bulb part cut off (dash-line), untreated with Collagenase V, showing compact ORS (arrow). D: Prepared hair with the bulb part cut off (dash-line), treated with Collagenase V, showing outgrown ORS with migrated cells outside of ORS (arrow). E: Outgrown, nearly confluent propagated cells outside of ORS on day 14 of culture. F: Primary culture of ORS cell pool developed from non-collagenised hairs on day 20. G: Primary culture of ORS cell pool developed from collagenised hairs on day 20. H: pure culture of selected melanocytes on day 26. I: Differentiated melanocytes in the pure culture at day 30.

FIGS. 3A-3F are exemplary images of the immunocytochemical characterization of the ORS culture. A: NKI\beteb is expressed in all epidermal melanocytes (NHEM); B: Tyrosinase is expressed in all epidermal melanocytes (NHEM); C: CD 90 is expressed in all non-melanocyte cells, prevalently fibroblasts; D: NKI\beteb is expressed in almost all ORS melanocytes (HM); E: Tyrosinase is expressed in almost all HM; F: absence of CD 90 expression in pure HM-culture.

FIGS. 9A-9D are exemplary images of both epidermal melanocytes (NHEM) and ORS melanocytes (HM) forming melanosomes. NKI/beteb labelling of melanosomes in NHEM and HM are depicted. A: NHEMs on 3 μm PCL scaffold, B: NHEMs on 10 μm PCL scaffold C: HM on 3 μm PCL scaffold D: HM on 10 μm PCL scaffold.

FIGS. 10A-10D are graphical representations of the relative melanin content and L-DOPA-tautomerase activity of NHEM and HM on PCL scaffolds and adherent surfaces. Black bars represent the NHEM and grey bars the HM. A: Melanin content in epidermal melanocytes on PCL scaffolds compared to an adherent surface. B: Melanin content in ORS melanocytes on PCL scaffolds compared to an adherent surface. C: L-DOPA activity in epidermal melanocytes on PCL scaffolds compared to an adherent surface. D: L-DOPA activity in ORS melanocytes on PCL scaffolds compared to an adherent surface.

FIGS. 11A-11B are exemplary images of outer root sheath melanocytes (HM ORS) embedded in the keratinocyte epidermal equivalent, which remain in the lower layer of the graft, equivalent to epidermal stratum basale, and express melanocyte markers. A: Epidermal melanocytes, normal light; B: Epidermal melanocytes, fluorescence.

FIGS. 12A-12H are exemplary images of immunocytochemical characterization of the various melanocyte cultures. A: NKI-beteb expression in normal human epidermal melanocytes (NHEM); B: Tyrosinase in epidermal melanocytes; C: CD-90 expression in pure dermal fibroblast culture; D: Lack of CD-90 expression in HM culture; E: HM in culture without L-DOPA addition; F: IBMX-mediated changes in HM morphology and increased melanin content, without L-DOPA; G: Melanin content upon L-DOPA substrate addition in HM; H: Increase in melanin content upon L-DOPA addition in IBMX-pre-treated HM.

DEFINITIONS

Figure 4:
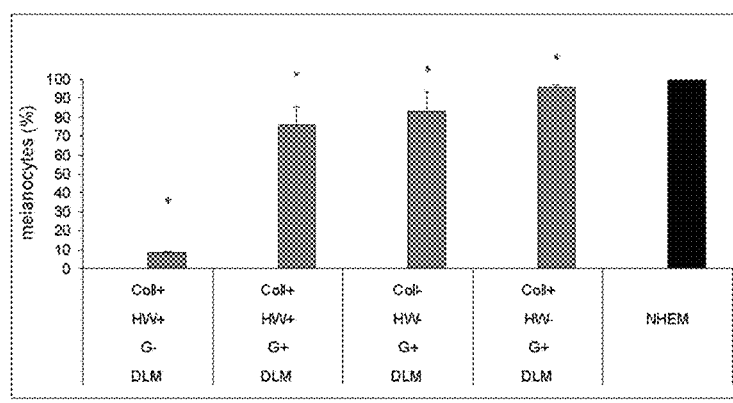
FIG. 4 is a graphical representation of the relative purity of an ORS melanocyte culture. The grey bars are showing the percentage of NKI/beteb-positive melanocytes in culture. Coll+/− corresponds to Collagenase V treatment, HW+ stands for presence of the bulb, HW− stands for absence of the bulb, G+/− stands for Geneticin treatment, DLM for DermaLife culture media applied. The black bar represents epidermal melanocyte control (differentiated NHEM), grown in a separate culture, showing 99% of NKI/beteb-expressing cells.

"Antibiotics" in context with the present invention refer to agents capable of inhibiting growth of microorganisms and/or inducing the death of microorganisms, such as bacteria or fungi, and/or as an additional selective agent for quickly-dividing cells. Suited antibiotics may be chosen by the skilled person. However, preferred antibiotics are selected from the group consisting of Penicillin, Amphotericin B, Gentamycine and Streptomycin or combinations thereof. A preferred combination of antibiotics is a Penicillin, Streptomycin, Amphotericin B and G-418 (also known as Geneticin).

"Hypoxic condition" refers to conditions with oxygen content below the normal atmospheric oxygen content. Hence in one embodiment step (ii) of the method for generating melanocytes from stem cells and/or melanocytes precursors is performed under conditions with an $O_2$ content of 20% or less, preferably 10% or less, even more preferably with an $O_2$ content of between 1% and 5%. In a preferred embodiment the cultivating steps of the method for producing an autograft, homograft or allograft is performed under conditions with an $O_2$ content of 5%, and a $CO_2$ content of 5%.

"Biocompatible carriers" in context of the present invention are carriers that can be transplanted to a human or animal body and provide a structure and biomechanical support that allows the cells to adhere to the surface. Furthermore, the skilled artisan will understand that the carriers shall be non-toxic, compatible with biological functions of the receiver and they are either tissue compatible and/or are biologically degradable in situ.

"Hypoxic condition" refers to conditions with oxygen content below the normal atmospheric oxygen content. Hence in one embodiment step (iv) of the method for producing an autograft, homograft or allograft is performed under conditions with an $O_2$ content of 20% or less, preferably 10% or less, even more preferably with an $O_2$ content of between 1% and 5%. In a preferred embodiment embodiment cultivating steps of the method for producing an autograft, homograft or allograft is performed under conditions with an $O_2$ content of 5%, and a $CO_2$ content of 5%.

"Normoxic condition" refers to conditions with oxygen content at the normal atmospheric oxygen content. Hence, in one embodiment the cultivation step(s) of the methods for producing an autograft, homograft or allograft is performed under conditions with an $O_2$ content of approximately 20%.

DESCRIPTION

In one embodiment the present invention relates to a method for generating melanocytes from stem cells comprising the steps of: removing the bulb of an epilated human hair;
i) incubating the remaining part of the epilated hair with a collagen degrading agent to release the stem cells from the outer root sheath;
ii) cultivating the separated stem cells from step (ii) in a differentiation medium that induces differentiation and stimulates growth of stem cells, melanocyte precursors and melanocytes, wherein the medium comprises one or more growth factors for differentiation into melanotic melanocytes; until only the differentiated melanotic melanocytes remain in the culture.

The inventors unexpectedly found that the yield and purity of melanocytes using the method according to the present invention can be greatly increased if the proximal part of the follicle/epilated human hair is cut off, i.e. the bulb. Hence, the method according to the present invention comprises removing the bulb of an epilated hair. The "bulb" of an epilated human hair in context of the present invention is the proximal part of the hair root, which contains mostly differentiated cells, predominantly fibroblast. In a preferred embodiment also the distal part of the hair shaft, also called 'the bulge' is cut off if not lost during epilation. In a preferred embodiment only the mid-part of the epilated hair root is used. The mid-part of an epilated hair in context with the present invention is preferably the morphological unit between the bulb (proximal part) and the sebaceous gland channel. This part contains a pool of heterogeneously differentiated cells, from pluripotent Neural-Crest-Like-Cells, over an array of partially differentiated precursors (epithelial, neuronal, adipocytic, chondrocytic, osteocytic to the fully differentiated cells, that are in majority epithelial precursors and serve for regeneration of epidermis. In context with the present invention the terms epilated hair and epilated hair follicle are used interchangeably.

The skilled artisan is able to adapt the amount of epilated hairs used in context with the present invention in order to adjust the total amount of generated melanocytes. In one embodiment the bulbs of 1 to 500 epilated hairs are removed in step (i) of the method for generating melanocytes from stem cells, preferably the bulbs of 10 to 80 epilated hairs are removed in step (i) of the method for generating melanocytes from stem cells, more preferably the bulbs of 30 to 60 epilated hairs are removed in step (i) of the method for generating melanocytes from stem cells.

In a preferred embodiment of the method for generating melanocytes from stem cells, the method comprises a further step between step (ii) and (iii) of washing the remaining part of the epilated hair with a washing solution after incubation with the collagen degrading agent.

Suitable washing solutions are well known in the art and can be chosen by those of skills in the art. In a preferred embodiment the washing solution is Dulbecco's Modified Eagle Medium (DMEM). In a further preferred embodiment the washing solution comprises an antibiotic, preferably selected from the group consisting of Gentamycin, Amphotericin B, Penicillin, Streptomycin, Neomycin, Carbenicillin, Penicillin G, Ampicillin, Polymyxin-B, tetracycline, Ciprofloxacin, Lincomycin, Spectinomycin, Cabenicilin, Thiostrepton, Ceftacidin, Apramycin, Vancomycin, Tobramycin, Rifampycin, and Hygromycin, preferably the washing solution comprises an antibiotic, preferably selected from the group consisting of Gentamycin, Amphotericin B, Penicillin, Streptomycin.

The skilled artisan is able to determine suited salts and/or concentrations of antibiotics for the washing solution. However, preferred antibiotics and preferred concentrations in brackets are given in the following: Penicillin, e.g. (50 U/ml to 150 U/ml, preferably 100 U/ml), Streptomycin-Sulfate (50 pg/ml to 20 mg/ml, preferably 100 µg/ml), Gentamycin-Sulfate (5 µg/ml to 3000 µg/ml, preferably 50 ug/ml), Amphotericin B (0.25 µg/ml to 30 µg/ml, preferably 2.5 µg/ml), (25 µg/ml to 600 µg/ml, preferably 50 µg/ml), (50 pg/ml to 10000 µg/ml, preferably 100 µg/ml), (25 µg/ml to 3000 µg/ml, preferably 50 ug/ml), Ampicillintrihydrat (50 U/ml to 200 U/ml, preferably 100 U/ml), -Carbenicillin, (50 U/ml to 200 U/ml, preferably 100 U/ml) (50 U/ml to 200 U/ml, preferably 100 U/mL), Polymyxin-B-Sulfate (25 µg/ml to 3000 µg/ml, preferably 100 µg/ml), (2 µg/ml to 80 µg/ml, preferably 10 µg/ml), 7-Hydroxy-Tetracyclin (each 2 to 25 µg/ml, preferably 5 µg/ml), (5 to 35 µg/ml, preferably 10 µg/ml), Erythromycin (50 µg/ml to 300 µg/ml, preferably 100 µg/ml), (2 µg/ml to 300 µg/ml, preferably 10 µg/ml), (2 µg/ml to 30 µg/ml, preferably 5 µg/ml), Ciprofloxacin (1 µg/ml to 10 µg/ml), Lincomycin (50 µg/ml), Spectinomycin) (5 µg/ml to 50 µg/ml, preferably 10 µg/ml), Carbenicilin (100 U/ml), Thiostrepton (25 µg/ml), Ceftacidin-Hydrate (100 µg/ml), Apramycin (2.5 µg/ml to 25 µg/ml), Vancomycin-Hydrochloride (100 µg/ml), Tobramycin (4 µg/ml to 100 µg/ml, preferably 80 µg/ml), Rifampycin (400 µg/ml), Hygromycin (200 µg/ml).

In a preferred embodiment the washing solution comprises Gentamycin, preferably at a concentration of 10 µg/ml to 100 µg/ml, more preferably at a concentration of 25 µg/ml to 75 µg/ml, even more preferably at a concentration of 50 µg/ml.

In a further preferred embodiment the washing solution comprises Amphotericin B, preferably at a concentration of 1 µg/ml to 20 µg/ml, more preferably at a concentration of 5 µg/ml to 15 µg/ml, even more preferably at a concentration of 10 µg/ml.

In a preferred embodiment the washing solution comprises two antibiotics, preferably Gentamycin and Amphotericin B.

In yet a further preferred embodiment the washing solution comprises DMEM, Gentamycin at a concentration of 50 µg/ml and Amphotericin B at a concentration of 10 µg/ml. In a most preferred embodiment the washing solution consists of DMEM, Gentamycin at a concentration of 50 µg/ml and Amphotericin B at a concentration of 10 µg/ml.

Collagen degrading agents are known by the skilled person. Collagen degrading agents in context of the present invention are all agents which digest collagen, a polymer consisting of protein, into smaller subunits. The inventors interestingly found that by the treatment with collagen degrading agents, cells of the Outer Root Sheath (ORS) are more easily separated from the rest of the hair root sheath cells during their cultivation. Digestion of collagen weakens the extracellular matrix and releases the cells, including stem cells, precursors and differentiated cells. In a preferred embodiment of the present invention the collagen degrading agent degrades a collagen selected from the group consisting of collagen I, collagen IV and collagen V. In a preferred embodiment the collagen degrading agent is an enzyme, preferably a collagenase. In a further preferred embodiment the collagen degrading agent is a collagenase selected from the group consisting of collagenase I, IV and V. He will recognize that collagen I, IV and V cover the cell surfaces, bases of cell basement membrane, the skin and the hair, respectively. The collagenases are preferably able to degrade more than one type of collagen. In a particularly preferred embodiment the collagen degrading agent is Collagenase V. In an even more preferred embodiment the collagen degrading agent is Collagenase V at a concentration of 5 mg/ml.

The skilled person is aware of suited compositions for the differentiation medium that induce differentiation and stimulate growth of stem cells, melanocyte precursors and melanocytes, wherein the medium comprises one or more growth factors for differentiation into functional melanotic melanocytes. Standard differentiation media known in the art can be used in the herein provided method. Exemplary differentiation media are described in Szabad et al. Arch. Derm. Res. (2007) 299:191-200, Kauser et al. Endocrinology (2005) 146 (2):532-543, http://lifelinecelltech.com/docs/SPM_DermaLife_M. Preferably, the differentiation medium to be used herein does not contain a tumor promoter (like Phorbol Myristate Acetate (PMA)). In a preferred embodiment the differentiation medium comprises a nutrient base, preferably selected from the group consisting of Dermalife medium (DLM) base of low bovine serum content (Life Line Cell Technology), Dulbeccos Modified Eagle Medium base (DMEM, Sigma-Aldrich), F12 Ham's nutrient mixture (Sigma-Aldrich), and PC-1 medium base (Lonza). In a preferred embodiment the differentiation medium comprises DermaLife medium (DLM) base as a nutrient base, more preferably DLM is the only nutrient base. It is particularly preferred that the collagen degrading agent is Collagenase V; and that the differentiation medium comprises DermaLife medium (DLM) base as a nutrient base, more preferably DLM is the only nutrient base comprised in the differentiation medium. The method according to the present invention unexpectedly allows the use of medium with a low or no serum content. Hence, it is preferred that the differentiation medium has a low serum content, preferably less than 2.5%, more preferably less than 2%, even more preferably less than 1%, yet more preferred 0.5% or less. It is even more preferred that the serum content of the differentiation medium is 0.5%. In a further embodiment the differentiation medium is serum free.

Further nutrients and additives may be applied. In a preferred embodiment the differentiation medium further comprises one or more compounds selected from the group consisting of β-adrenergic receptor ligands, such as epinephrine and derivatives thereof, $Ca^{2+}$, L-glutamine, insulin, Vitamin C, calf serum, Epidermal Growth Factor (EGF), basic Fibroblast Growth factor and its variants bFGF/FGF2, Endothelin-1, α-Melanocyte Stimulating Hormone (α-MSH), Hydrocortisone, Stem Cell Factor (SCF), Nerve Growth Factor beta (NGF-β), Hepatocyte Growth Factor (HGF), StiMel factor cocktail (Life Line Cell Technology), and antibiotics. In a preferred embodiment the differentiation medium comprises DermLife medium (DLM) base as a nutrient base, and one or more compounds selected from the group consisting of β-adrenergic receptor ligands, such as epinephrine and derivatives thereof, $Ca^{2+}$, L-glutamine, insulin, Vitamin C, calf serum, Epidermal Growth Factor (EGF), basic Fibroblast Growth factor and its variants bFGF/FGF2, Endothelin-1, α-Melanocyte Stimulating Hormone (α-MSH), Hydrocortisone, Stem Cell Factor (SCF), Nerve Growth Factor beta (NGF-β), Hepatocyte Growth Factor (HGF), StiMel factor cocktail (Life Line Cell Technology), and antibiotics, preferably DLM is the only nutrient base comprised in the differentiation medium and the differentiation medium comprises one or more compounds selected from the group consisting of β-adrenergic receptor ligands, such as epinephrine and derivatives thereof, $Ca^{2+}$, L-glutamine, insulin, Vitamin C, calf serum, Epidermal Growth Factor (EGF), basic Fibroblast Growth factor and its variants bFGF/FGF2, Endothelin-1, α-Melanocyte Stimulating Hormone (α-MSH), Hydrocortisone, Stem Cell Factor (SCF), Nerve Growth Factor beta (NGF-β), Hepatocyte Growth Factor (HGF), StiMel factor cocktail (Life Line Cell Technology), and antibiotics. Furthermore, in a preferred embodiment the collagen degrading agent is Collagenase V; and the differentiation medium comprises DermLife medium (DLM) base as a nutrient base and one or more compounds selected from the group consisting of β-adrenergic receptor ligands, such as epinephrine and derivatives thereof, $Ca^{2+}$, L-glutamine, insulin, Vitamin C, calf serum, Epidermal Growth Factor (EGF), basic Fibroblast Growth factor and its variants bFGF/FGF2, Endothelin-1, α-Melanocyte Stimulating Hormone (α-MSH), Hydrocortisone, Stem Cell Factor (SCF), Nerve Growth Factor beta (NGF-β), Hepatocyte Growth Factor (HGF), StiMel factor cocktail (Life Line Cell Technology), and antibiotics, preferably DLM is the only nutrient base comprised in the differentiation medium and the differentiation medium further comprises one or more compounds selected from the group consisting of β-adrenergic receptor ligands, such as epinephrine and derivatives thereof, $Ca^{2+}$, L-glutamine, insulin, Vitamin C, calf serum, Epidermal Growth Factor (EGF), basic Fibroblast Growth factor and its variants bFGF/FGF2, Endothelin-1, α-Melanocyte Stimulating Hormone (α-MSH), Hydrocortisone, Stem Cell Factor (SCF), Nerve Growth Factor beta (NGF-β), Hepatocyte Growth Factor (HGF), StiMel factor cocktail (Life Line Cell Technology), and antibiotics.

The further nutrients and additives may be applied in suited concentrations well known in the art. However, preferred concentrations are given below:

In a preferred embodiment the differentiation medium comprises L-Glutamine, preferably at a concentration of 3 mM to 10 mM, more preferably 4 mM to 8 mM, yet more preferably 5 mM to 7 mM, even more preferred the differentiation medium comprises L-Glutamine at a concentration of 6 mM.

In a further preferred embodiment the differentiation medium comprises insulin, preferably at a concentration of 1 µg/ml to 10 µg/ml, more preferably at a concentration of 2 µg/ml to 8 µg/ml, yet more preferably at a concentration of 4 µg/ml to 6 µg/ml, even more preferred the differentiation medium comprises insulin at a concentration of 5 µg/ml.

In a further preferred embodiment the differentiation medium comprises Vitamin C, preferably at a concentration of 10 µg/ml to 100 µg/ml, more preferably at a concentration of 20 µg/ml to 80 µg/ml, yet more preferably at a concentration of 40 µg/ml to 60 µg/ml, even more preferred the differentiation medium comprises Vitamin C at a concentration of 50 µg/ml.

In another preferred embodiment the differentiation medium comprises Epinephrin, preferably at a concentration of 0.1 µM to 5 µM, more preferably at a concentration of 0.3 µM to 2.5 µM, yet more preferably at a concentration of 0.5 µM to 1.5 µM, even more preferred the differentiation medium comprises Epinephrin at a concentration of 1 µM.

In another preferred embodiment the differentiation medium comprises Calcium chloride, preferably at a concentration of 0.1 mM to 0.4 mM, more preferably at a concentration of 1.5 mM to 2.5 mM, even more preferred the differentiation medium comprises Calcium chloride at a concentration of 0.2 mM.

In another preferred embodiment the differentiation medium comprises Bovine Pituitary Extract, preferably at a concentration of 10 µg/ml to 40 µg/ml, more preferably at a concentration of 15 µg/ml to 35 µg/ml, even more preferred the differentiation medium comprises Bovine Pituitary Extract at a concentration of 25 µg/ml.

In another preferred embodiment the differentiation medium comprises Basic Fibroblast Growth factor bFGF/FGF2, preferably at a concentration of 1 ng/ml to 20 ng/ml, more preferably at a concentration of 5 ng/ml to 15 ng/ml, even more preferred the differentiation medium comprises Basic Fibroblast Growth factor bFGF/FGF2 at a concentration of 10 ng/ml.

In another preferred embodiment the differentiation medium comprises Epidermal Growth Factor EGF, preferably at a concentration of 0.2 ng/ml to 20 ng/ml, more preferably at a concentration of 1.5 ng/ml to 5 ng/ml, even more preferred the differentiation medium comprises Epidermal Growth Factor EGF at a concentration of 2.5 ng/ml.

In another preferred embodiment the differentiation medium comprises Endothelin, preferably at a concentration of 0.2 ng/ml to 20 ng/ml, more preferably at a concentration of 1 ng/ml to 10 ng/ml, even more preferred the differentiation medium comprises Endothelin at a concentration of 5 ng/ml.

In a further preferred embodiment the differentiation medium comprises StiMel factor cocktail (Life Line Scientific Inc.), preferably at a concentration of 0.1% to 5%, more preferably at a concentration of 0.3 µM to 2.5 µM, yet more preferably at a concentration of 0.5% to 1.5%, even more preferred the differentiation medium comprises StiMel factor cocktail at a concentration of 1%.

In a further preferred embodiment the differentiation medium does not comprise cholera toxin. In another embodiment the differentiation medium does not comprise tumor promoters, such as phorbol-12-myristate 13-acetate (PMA, TPA). In a preferred embodiment the differentiation medium does neither comprise cholera toxin nor a tumor promoter, such as phorbol-12-myristate 13-acetate (PMA, TPA).

In a preferred embodiment the differentiation medium comprises Penicillin, preferably at a concentration of 1.000 units/ml to 20.000 units/ml, more preferably at a concentration of 5.000 units/ml to 15.000 units/ml, yet more preferred the differentiation medium comprises Penicillin at a concentration of 10.000 units/ml.

In a preferred embodiment the differentiation medium comprises Amphotericin B, preferably at a concentration of 1 µg/ml to 20 µg/ml, more preferably at a concentration of 5 µg/ml to 10 µg/ml, yet more preferred the differentiation medium comprises Amphotericin B at a concentration of 10 µg/ml.

In a very preferred embodiment the differentiation medium comprises Gentamycin, preferably at a concentration of 10 µg/ml to 100 µg/ml, more preferably at a concentration of 25 µg/ml to 75 µg/ml, even more preferably at a concentration of 50 µg/ml.

In another preferred embodiment the differentiation medium comprises Penicillin, Streptomycin and Amphotericin. In a most preferred embodiment the differentiation medium comprises Penicillin at a concentration of 10.000 units/ml, Streptomycin at a concentration of 10.000 µg/ml, and Amphotericin B at a concentration of 25 µg/ml.

In a particularly preferred embodiment the differentiation medium is DLM and comprises Penicillin, Streptomycin and Amphotericin. In a most preferred embodiment the differentiation medium comprises Penicillin at a concentration of 10.000 units/ml, Streptomycin at a concentration of 10.000 µg/ml, and Amphotericin B at a concentration of 25 µg/ml.

In another particularly preferred embodiment the differentiation medium base is Dulbecco's Modified Eagle Medium DMEM with a known formulation disclosed in Dulbecco, R and Freeman, G. (1959) Virology 8:396), even more preferably DMEM 5030, produced by Sigma® in GMP-grade quality.

During differentiation the medium may be exchanged as desired. The skilled person knows when and how to change the medium. In a preferred embodiment the medium is changed during differentiation every 2 days.

The skilled person may choose suited combinations and concentrations for the differentiation medium. However, some preferred combinations and concentrations are given below.

In a preferred embodiment DermaLife differentiation medium purchased from Life Line Cell Technology is used as the differention medium, which comprises DLM medium base of low bovine serum content (0.5%), L-Glutamine (6 mM), Insulin (5 µg/ml), Vitamin C (50 µg/ml), Epinephrin (1 µM), StiMel factor cocktail (1%) and Antimicrobial supplement (Penicillin 10.000 units/ml, Streptomycin 10.000 µg/ml, and Amphotericin B 25 µg/ml). In another embodiment the differentiation medium comprises DLM medium base of low bovine serum content (0.5%), L-Glutamine (6 mM), Insulin (5 µg/ml), Vitamin C (50 µg/ml), Epinephrin (1 µM), StiMel factor cocktail (1%) (mixture of growth factors, LifeLine Technology) and Gentamycine (50 µg/ml).

In a further preferred embodiment DermaLife differentiation medium purchased from Life Line Cell Technology is used as the differentiation medium, which comprises DLM medium base of low bovine serum content (0.5%), L-Glutamine (6 mM), Insulin (5 µg/ml), Vitamin C (50 µg/ml), Epinephrin (1 µM), StiMel factor cocktail (1%) and Gentamycine (50 µg/ml). In another embodiment the differentiation medium comprises DLM medium base of low bovine serum content (0.5%), L-Glutamine (6 mM), Insulin (5 µg/ml), Vitamin C (50 µg/ml), Epinephrin (1 µM), and StiMel factor cocktail (1%) (mixture of growth factors, LifeLine Technology).

In yet another preferred embodiment the differentiation medium comprises DLM basal medium, L-Glutamine (6 mM), $Ca^{2+}$ (0.2 mM), Insulin (5 µg/ml), Vitamin C (50 µg/ml), Epinephrin (1 µM), and/or EGF (1 ng/ml), and/or bFGF/FGF2 (10 ng/ml), and/or Endothelin-1 (20 nM), and/or α-MSH (5 nM), and/or Hydrocortison (0.5 µg/ml), and/or SCF (10 ng/ml), and/or NGF-β (20 ng/ml), and/or HGF (10 ng/ml), and/or Gentamycin (50 µg/ml).

In yet another preferred embodiment the differentiation medium comprises serum-free PC-1 medium base and/or DMEM and/or F12, 1-10% human serum, L-Glutamin (6 mM), $Ca^{2+}$ (0.2 mM), Insulin (5 µg/ml), Vitamin C (0.2%), Epinephrin (0.2%), EGF (1 ng/ml), and/or bFGF/FGF2 (10 ng/ml), Endothelin-1 (20 nM), and/or α-MSH (5 nM), Hydrocortison (0.5 µg/ml), SCF (10 ng/ml), and/or NGF-β 20 ng/ml), and HGF (10 ng/ml), Gentamycin (f.c. 50 µg/ml).

In yet another preferred embodiment the differentiation medium comprises DMEM basal medium, L-Glutamine (6 mM), $Ca^{2+}$ (0.2 mM), Insulin (5 µg/ml), Vitamin C (50 µg/ml), Epinephrin (1 µM), and/or EGF (1 ng/ml), and/or bFGF/FGF2 (10 ng/ml), and/or Endothelin-1 (20 nM), and/or α-MSH (5 nM), and/or Hydrocortisone (0.5 µg/ml), and/or SCF (10 ng/ml), and/or NGF-β (20 ng/ml), and/or HGF (10 ng/ml), and/or Gentamycin (50 µg/ml).

In yet another preferred embodiment the differentiation medium comprises DMEM medium base, 1-10% human serum, L-Glutamine (6 mM), $Ca^{2+}$ (0.2 mM), Insulin (5 µg/ml), Vitamin C (0.2%), Epinephrine (0.2%), EGF (1 ng/ml), and/or bFGF/FGF2 (10 ng/ml), Endothelin-1 (20 nM), and/or α-MSH (5 nM), and/or Hydrocortisone (0.5 µg/ml), and/or SCF (10 ng/ml), and/or NGF-β 20 ng/ml), and HGF (10 ng/ml), Gentamycin (f.c. 50 µg/ml).

In yet another preferred embodiment the differentiation medium comprises DMEM medium base, 1-10% human serum, L-Glutamine (6 mM), $Ca^{2+}$ (0.2 mM), Bovine Pituitary Extract (25 µg/ml), Insulin (5 µg/ml), Vitamin C (0.2%), Epinephrine (0.2%), EGF (1 ng/ml), bFGF/FGF2 (10 ng/ml), Epidermal Growth Factor EGF (2.5 ng/ml), Endothelin-1 (20 nM), Gentamycin (50 µg/ml).

In an even more preferred embodiment the differentiation medium comprises DMEM medium base, 5% human serum, L-Glutamine (6 mM), $Ca^{2+}$ (0.2 mM), Bovine Pituitary Extract (25 µg/ml), Insulin (5 µg/ml), Vitamin C (0.2%), Epinephrine (0.2%), EGF (1 ng/ml), bFGF/FGF2 (10 ng/ml), Epidermal Growth Factor EGF (2.5 ng/ml), Endothelin-1 (20 nM), Gentamycin (50 µg/ml).

Growth factors and cultivation agents suited for the method according to the present invention are known by those skilled in the art and can be adapted according to the needs. Preferably these growth factors and cultivation agents trigger the differentiation of stem cells to melanocytes, or at least do not interfere with the melanocyte differentiation process and favorize the growth and up-scaling of melanocytes. However, in one embodiment of the method for generating melanocytes according to the present invention the growth factors and cultivation agents are selected from the group consisting of ethanolamine, phosphoethanolamine, hydrocortisone, basic fibroblast growth factor (bFGF), dibutyryl cyclic adenosine monophosphate (db-cAMP), melanocyte growth factor (MeGF), Kaposi's sarcoma derived FGF-like factor (hst/K-FGF), hepatocyte growth factor (HGF), stem cell growth factor (SCF), endothelin-1, alpha-melanocyte stimulating hormone (α-MSH) and mixtures of native factors from the medium conditioned by cultured human keratinocytes, or from bovine pituitary extract (BPE), or bovine brain extract (Wilkins et al. 1985).

In a preferred embodiment the differentiation step (ii) of the method for generating melanocytes from stem cells and/or melanocytes precursors is performed under hypoxic conditions or normoxic conditions. More preferably, the differentiation step is performed under hypoxic conditions.

Furthermore, in a preferred embodiment the differentiation step (ii) is performed at a medium-air interface. The skilled artisan knows how to perform differentiation at a medium-air interface. Preferably the remaining part of the epilated hair follicle of step (i) is placed on mesh, preferably a nylon mesh, wherein the nylon mesh is in contact with the differentiation medium. Preferred nylon meshes have a pore size of 1 µm or less, preferably 0.5 µm or less, more preferred the nylon mesh has a pore size of 0.4 µm. In a most preferred embodiment the medium-air interface is generated by placing the epilated hair follicle of step (i) on a 24 mm Transwell® nylon-meshe with 0.4 µm Pore Polyester Membrane Insert (Corning) and grown in medium-air-interface conditions. In a preferred embodiment of the medium-air interface the remaining part of the epilated hair follicle of step (i) are incubated under hypoxic conditions, preferably they are he exposed to a hypoxic gas mixture. The hypoxic gas mixture preferably has a partial $O_2$ gas pressure of 5%, more preferably the hypoxic gas mixture further has a partial $CO_2$ gas pressure of 5%, most preferred the hypoxic gas mixture has a $O_2$ gas pressure of 5%, a partial $CO_2$ gas pressure of 5%, and a $N_2$ partial gas pressure of 90%.

The inventors unexpectedly found that the cultivation step (iii) of the method for generating melanocytes according to the present invention may be performed until all other cells disappear as the medium is selective for the generation of melanocytes from the stem cells. The other cell types are interestingly selected away and only the melanocytes remain. Hence, in one embodiment of the present invention step (iii) is performed until at least 85% of the cells are differentiated melanocytes, preferably at least 95%, more preferably 99%, even more preferably until all of the cells are differentiated melanocytes.

The skilled artisan knows methods to determine whether cells are differentiated melanocytes. For example the skilled artisan can determine whether cells express the melanocyte markers and not fibroblast markers. Known melanocytes markers are for example Tyrosinase, glycoprotein 100 (gp100) variants, calcium-binding S100 proteins, Microphtalmia-associated Transcription Factor (MITF) as genes characteristically expressed in melanocytes; further on, DOPA-tautomerase activity and subsequent melanin content are reliable markers of melanocyte function. Fibroblast markers are for example Cluster of Differentiation 90 cell surface protein (CD-90), Cluster of Differentiation 34 (CD34), Fibroblast Surface Antigen (SFA), Heat Shock Protein 47 (HSP47). Fully differentiated melanocytes and fibroblasts also assume characteristic morphology.

However, in one embodiment of the method for generating melanocytes according to the present invention the method comprises a further step (iv) selecting and isolating the differentiated melanocytes in the culture.

In accordance with the above, herein provided is a method for generating melanocytes from stem cells comprising the steps of:
  (i) removing the bulb of an epilated human hair;
  (ii) incubating the remaining part of the epilated hair with a collagen degrading agent to separate stem cells from the outer root sheath;

(iii) cultivating the separated stem cells from step (ii) in a medium that induces differentiation and stimulates growth of stem cells, melanocyte precursors and melanocytes, wherein the medium comprises one or more growth factors for differentiation into melanotic melanocytes, (iv) isolating the differentiated melanotic melanocytes in the culture, wherein melanocytes are isolated in step (iv) using anatomic selection of hair root subsections. Step (iv) may comprise, in the alternative or in addition to using anatomic selection of hair root subsections, differential trypsinization. Step (iv) may, in the alternative or in addition to using anatomic selection of hair root subsections, and/or in the alternative or in addition to differential trypsinization, G-418 (Geneticin) treatment.

As mentioned above, the step of incubating the remaining part of the epilated hair with a collagen degrading agent to separate stem cells from the outer root sheath according to the herein provided method can contain releasing/migrating/leaving of the stem cells from e.g. the extracellular matrix.

Provided is a method for generating melanocytes from stem cells comprising the steps of:
1. removing the bulb of an epilated human hair;
2. incubating the remaining part of the epilated hair with a collagen degrading agent to separate stem cells from the outer root sheath;
3. cultivating the separated stem cells from step (ii) in a medium that induces differentiation and stimulates growth of stem cells, melanocyte precursors and melanocytes, wherein the medium comprises one or more growth factors for differentiation into melanotic melanocytes,
    a. selecting the differentiated melanotic melanocytes in the culture, wherein the step of selecting comprises G-418 (Geneticin) treatment.

The step of selection and/or isolation in the herein provided method may comprise isolating the melanocytes using differential trypsinization and subsequently G-418 (Geneticin) treatment. In other words, the step of selection and/or isolation in the herein provided method may comprise isolating the melanocytes using G-418 (Geneticin) treatment along with differential trypsinization.

Different methods are known to select and isolate differentiated melanotic melanocytes from cultures. Methods of differential trypsinization or G-418 (Geneticin) treatment are known methods (In Vitro. 1984 May; 20(5):447-50, Exp Cell Res. 1982 December; 142(2):309-15, Proc Natl Acad Sci USA. 1982 March; 79(6):2018-22). The skilled artisan is aware of these methods. However, the inventors unexpectedly found that the purity and amount of melanocytes obtained by the above-outlined method can be further enhanced by using differential trypsinization and/or G-418 (Geneticin) treatment. Hence, in one embodiment of the method for generating melanocytes according to the present invention melanotic melanocytes are isolated in step (iv) using differential trypsinization and/or G-418 (Geneticin) treatment. The inventors now unexpectedly found that the selection and isolation of differentiated melanotic melanocytes is greatly enhanced if both methods are performed, preferably the differential trypsinization is performed at every passage of the cell culture, whereas the G-418 (Geneticin) treatment is applied once in the course of 24 to 48 hours, preferably once in the course of 48 hours. In one embodiment of the present invention the melanotic melanocytes are isolated using differential trypsinization combined with a single G-418 (Geneticin) treatment.

Differential trypsinization is known by those skilled in the art. In one embodiment of the differential trypsinization the cells are washed with a buffer and challenged with Trypsin and Ethylenediaminetetraacetic acid (EDTA). In a more preferred embodiment of the trypsinization the cells are washed with HEPES buffer and challenged with 0.04% Trypsin/0.03% EDTA for 4 minutes. The 4 minutes represent the time sufficient for melanocytes to withdraw their dendrites under the stimulus of trypsin and detach from the polystyrene surface of the cell culture vessel. Fibroblasts and keratinocytes adhere to the surface with their large soma and therefore with more adherence force, and they are more robust to the stress stimuli altogether, therefore they need longer exposure to trypsin than the melanocytes and still remain adherent after 4 minutes of trypsin digestion. The supernatant with loose trypsinized pure melanocytes is taken into the next passage of the culture and cultivated further.

G-418 (Geneticin) treatment is known by those skilled in the art. G-418, also known as Geneticin, is an antibiotic, a known inhibitor of the 80S ribosomes and thereby of protein synthesis. Exposure to Geneticin has most impact on the fast-dividing cells with large need for protein synthesis, in case of the ORS primary culture keratinocytes and fibroblasts, which happen to be the major contaminants of the targeted melanocyte culture. On the other hand, the melanocytes are slow-dividing and therefore quite immune to Geneticin stress, therefore, they all survive the Geneticin treatment that takes up to 48 hours. Upon this procedure, one can observe healthy adherent melanocytes and apoptotic and necrotic rounded half-loose fibroblasts and keratinocytes in the treated culture. The detached majority of the out-selected fibroblasts and keratinocytes are flushed away with HEPES buffer and those that remain attached do not survive and are hereby seceded within the next passage. In one embodiment Geneticin is applied for 12 h to 48 h, preferably for 24 h to 48 h, more preferably for about 24 h, yet more preferably for about 48 h. The skilled artisan will be able to decide on the time for which Geneticin is applied. This treatment blocks translation of the eukaryotic cells. The cells that divide quickly are much more sensitive to Geneticin, since they have a very active protein production (and hereby a very intensive translation). The inventors found that fibroblasts and keratinocytes divide quickly and they are selected away, whereas the melanocytes divide slowly and survive the selection. Hence, the skilled artisan can decide on the time for which the cells are treated with Geneticin by monitoring the amount of fibroblasts and keratinocytes and establish an optimal time of treatment based on that.

Furthermore, it has been demonstrated herein that the herein provided method allows the advantageous and improved generation of melanocytes. Following the medium-air-interface cultivation of follicles as described herein (see e.g. method section of Example 1) the melanocytes can be further cultivated in adherent culture and regularly passaged. Accordingly, the herein provided method can advantageously comprise adherent culture of melanocytes. The herein provided method can further comprise passaging of melanocytes.

For example, the melanocytes can be passaged 1, 2, 3, 4, 5, 6, or more times (and up to 15 times to increase the melanocyte number or yield. "Passaging" means that a certain number of cells (e.g. sufficient to cover more than 10% of the cell vessel surface, preferably 100.000 cells per 25 cm$^2$ vessel) are taken from a first medium-air-interface follicle culture which has been produced in accordance with the present invention. These cells are cultivated under adherent culture conditions described herein, like adherent culture in Example 1. When the cells proliferate and reach more than 80% confluence on given surface, they are detached by trypsin and taken to a larger vessel surface. This procedure/cycle is called herein passaging.

This procedure can be performed many times to maintain a melanocyte population for a long period of time. This procedure can also be used to produce melanocytes in accordance with the present invention.

The present invention provides melanocytes obtainable or obtained by the herein provided method for generating melanocytes. As shown in the appended examples, the melanocytes (also referred to herein as human hair follicle melanocytes, or short "HM") obtained in accordance with the present invention have features which are characteristic of melanocytes, like characteristic dendritic morphology, expression of marker proteins (e.g. Tyrosinase, variants of gp100 protein, NKI-beteb, HMB45. Further, the herein provided melanocytes show reaction to isobutyl-methylxanthine (IBMX). They also show activity of Tyrosinase, CDT/TRP-2, and TRP-1, utilised in converting L-DOPA into melanin as well as spontaneous melanin production. The melanocytes display melanin content and are characterized by the absence of a CD90 signal/expression. Due to these characteristic features, the herein provided melanocytes (HM) are a good substitute for normal human epidermal melanocytes (NHEM); see Example 1 and 3. Yet, the herein provided melanocytes also show important differences compared to other melanocyte cells, like NHEM. For example, the melanocytes obtainable by the herein provided method have different cell surface markers as compared to NHEM. Due to these different surface markers, the herein provided melanocytes can easily be distinguished from e.g. NHEM cells by routine methods, like FACS, as demonstrated in Example 3.

Figure 17:
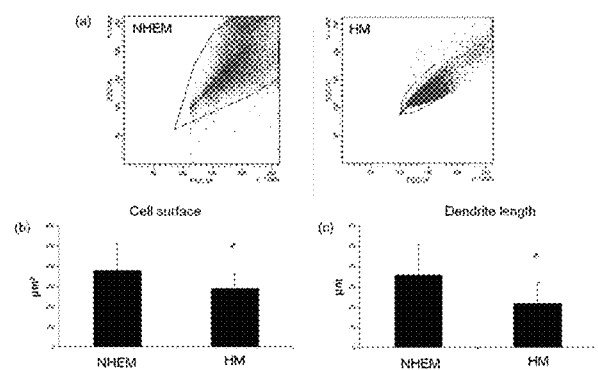
FIG. 17 is a graphical representation of the different sizes of cell soma and dendrite length in NHEM and HM. A: Relative cell size of NHEM and HM measured by Forward Scatter Plot (x-axis); B: Cell size of NHEM and HM in $\mu m^2$; C: Dendrite length of NHEM and HM in μm.

Furthermore, the melanocytes obtainable by the method of the invention have a smaller soma and shorter dendrites than other melanocytes, like adult skin melanocyte cells, such as NHEM; see Example 3 and FIG. 17. Also the number of dendrites is slightly lower in the melanocytes obtainable by the method of the invention compared with other melanocytes, like adult skin melanocyte cells, such as NHEM. Cell surface of NHEM is in average 23% larger than that of melanocytes of the present invention (HM cells) and their dendrites are 39% longer. Also, NHEM tend to have more dendrites than HM in average.

NHEM cells display an average surface of 377±135 µm$^2$, whereas the HM display 290±74 µm$^2$; hereby, NHEM soma is 23% larger in surface than HM soma (p=0.0451). Accordingly, the melanocytes obtainable by the method of the invention have an average smaller surface or soma than other melanocytes, like adult skin melanocyte cells, such as NHEM. The average surface or soma of the melanocytes obtainable by the method of the invention is at least 5, 6, 7, 8, 9, 10, 11, 12, 13, 14, 15, 16, 17, 18, 19, preferably at least 20% smaller than the average surface or soma of other melanocytes, like adult skin melanocyte cells, such as NHEM.

Dendrites of NHEM are in average 35.73±15 µm long, which is 39% longer than the 21.57±10 µm long dendrites of the melanocytes obtainable by the method of the invention (HM cells) (p=0.045). Accordingly, the melanocytes obtainable by the method of the invention have shorter dendrites on average than other melanocytes, like adult skin melanocyte cells, such as NHEM. The average dendrite of the melanocytes obtainable by the method of the invention is at least 10, 15, 20, 25, 30, 31, 32, 33 or 34, preferably at least 35% shorter than the average dendrite of other melanocytes, like adult skin melanocyte cells, such as NHEM.

Furthermore, as shown in Example 3, NHEM have a slightly higher average number of dendrites (3.13±1.19) than HM (2.47±0.64), (p=0.065, non-significant).

Table 5 provided herein further below shows a comprehensive summary of markers characteristic for melanocytes obtainable or obtained by the method of the present invention (a "+" indicates presence/expression of the marker). The melanocytes obtainable or obtained by the method of the present invention may express one or more of said markers of Table 5. In other words, the herein provided melanocytes may express one marker alone or in combination with any one of the other markers (i.e. in combination with one or more of the other markers).

Table 3 provides markers which are expressed/present in the herein provided melanocytes and which are not expressed/present in NHEM cells. Also in this context, the herein provided melanocytes may express one marker alone or in combination with any one of the other markers (i.e. in combination with one or more of the other markers) of Table 3. As described herein, the presence of one a marker alone or in combination with other marker(s) can be determined/analysed.'

As shown herein, the melanocytes obtainable in accordance with the invention express one or more well-known marker genes as exemplified in the Table 3 and 5 herein. Non-limiting examples of such marker genes are CD1a, CD28, CD77, CD79b, CD137 Ligand, CD140a, CD140b, CD282, HLA-A2, HLA-DQ, CD104, CD106, CD142.

It is preferred that the herein provided and described melanocytes express at least one of the above genes alone or in combination with one or more of these or further marker genes as exemplified in Table 3 and 5.

The nucleic acid or protein sequences of these marker genes to be used herein may be deduced from the respective databases like NCBI. The tables also provide accession numbers of the respective database.

The denomination "+" (e.g. CD1a+) indicates the presence of the respective marker, i.e. indicates an expression of the marker that may be reflected in a detectable expression level (protein, mRNA etc.) of this marker gene. Generally, a cell is classified as "melanocyte" obtainable or obtained by the herein provided method if at least one of the herein described marker genes is present at a detectable expression level. Methods for detecting and evaluating expression levels of such genes are well known in the art and are also demonstrated in the appended examples. Accordingly the melanocytes obtainable by the herein provided method can be melanocytes (CD1a+, CD28+, CD77+, CD79b+, CD137 Ligand+, CD140a+, CD140b+, CD282+, HLA-A2+, HLA-DQ+, CD104+, CD106+, and/or CD142+).

For example, the protein expression level can be detected by taking advantage of FACS, immunoagglutination, immunoprecipitation (e.g. immunodiffusion, immunelectrophoresis, immune fixation), western blotting techniques, (in situ) immunohistochemistry, (in situ) immunocytochemistry, affinity chromatography, enzyme immunoassays, and the like. These and other suitable methods of contacting proteins are well known in the art and are, for example, also described in Sambrook and Russell (2001), Molecular Cloning: A Laboratory Manual, CSH Press, Cold Spring Harbor, N.Y., USA; Burke et al. (1990), Methods in Yeast Genetics, A Laboratory Course Manual, Cold Spring Harbor Laboratory Press, 1990.)

If the gene product is an mRNA, contacting and binding can be performed by taking advantage of Northern blotting techniques or PCR techniques, like in-situ PCR. These and other suitable methods for binding (specific) mRNA are well known in the art and are, for example, described in Sambrook and Russell (2001, loc. cit.).

Quantification of the protein level can be performed by taking advantage of the techniques referred to above, in particular Western blotting techniques. Generally, the skilled person is aware of methods for the quantitation of polypeptides. Amounts of purified polypeptide in solution can be determined by physical methods, e.g. photometry. Methods of quantifying a particular polypeptide in a mixture rely on specific binding, e.g of antibodies. Specific detection and quantitation methods exploiting the specificity of antibodies comprise for example immunohistochemistry (in situ). Western blotting combines separation of a mixture of proteins by electrophoresis and specific detection with antibodies. Electrophoresis may be multi-dimensional such as 2D electrophoresis. Usually, polypeptides are separated in 2D electrophoresis by their apparent molecular weight along one dimension and by their isoelectric point along the other direction.

Quantification of the level of the gene product, in particular RNA/mRNA can be performed by taking advantage of Northern blotting techniques, hybridization on microarrays or DNA chips equipped with one or more probes or probe sets specific for mRNA transcripts or PCR techniques referred to above, like, for example, quantitative PCR techniques, such as Real Time PCR. A skilled person is capable of determining the amount of the component, in particular said gene products, by taking advantage of a correlation, preferably a linear correlation, between the intensity of a signal and the amount of the component to be determined.

A person skilled in the art is easily in the position to determine the expression level of the herein described marker genes based on his common general knowledge and the teaching provided herein. In particular, a skilled person can readily decide whether a certain marker is or is not expressed in a melanocyte obtainable by the herein provided method.

An exemplary method to be used herein and used in the appended examples for determining expression of surface proteins, is based on combination of fluorophore-labelled antibody binding and analysis by flow cytometry. The method is based on running a single-cell suspension through a capillary exposed to a laser beam. Diffraction off the side of the cell walls (Forward Scatter, FSC) and through its intracellular content (Side Scatter, SSC) can be quantified and interpreted as relative size (FSC readout) or complexity (SSC readout). Both readouts can be plotted on x and y axis of a graph to define basic morphological parameters read out at the beginning of the analysis (FIG. 17, a). Forward- and Side Scatter measurements are independent of the fluorescent signal. Fluorescent signal itself is directly proportional to the number of attached fluorophores, in the case described in Example 3: surface receptor markers labelled with fluorescing antibody (FIG. 17, b). High-throughput measuring flow-cytometer devices such as BD FACS-Array, used in Example 3, allow quick measurement of antibody panels without a risk of fluorophore fadeout or loss.

The principle and methodology of cell surface marker analysis used herein is demonstrated and described in Example 3 (see e.g. Methods section thereof)

The inventors unexpectedly found that the melanocytes derived by the methods for obtaining melanocytes according to the present invention show extraordinarily good properties as graft constituents. Hence, the present invention further relates to a method for producing an autograft, homograft or an allograft comprising melanocytes, said method comprising the steps of:
  (i) providing a suspension comprising melanocytes obtainable by a method for generating melanocytes from stem cells according to the present invention;
  (ii) providing a biocompatible carrier; and
  (iii) cultivating the melanocytes on said biocompatible carrier.

The suspension comprising the melanocytes may further comprise fibrin, thrombin, or both.

The melanocytes may be further applied along the following routes: in the form of liquid suspension, as an aerosol (spray), grown on a biocompatible carrier as a single melanocyte culture or combined with keratinocytes to form an epidermal equivalent or as a cellular epidermal equivalent, composed of a basal melanocyte layer and stratified keratinocytes. In a further embodiment the melanocytes may be combined with fibroblasts and keratinocytes to form a dermal equivalent comprising melanocytes, keratinocytes and fibroblasts.

In one embodiment the autograft, homograft or allograft to be produced by the method according to the present invention comprises keratinocytes.

Methods for obtaining and/or stratifying keratinocytes are known by those skilled in the art. However, the keratinocytes may be applied with the melanocytes in different ways. For example, the keratinocytes may be comprised in the resulting autograft, homograft or allograft. Hence, in one embodiment of the method for producing an autograft, homograft or allograft according to the present invention the method further comprises step (iv) stratifying keratinocytes on the melanocytes cultivated on said biocompatible carrier; and step (v) cultivating said keratinocytes on the biocompatible carrier comprising the melanocytes. Furthermore, the keratinocytes may be provided separately, e.g. as a suspension or spray, optionally on a further biocompatible carrier.

The inventors found that the melanocytes may be applied to the area to be treated in different ways. For example, a solid autograft, homograft or allograft may be used. In this case the biocompatible carrier used in the method for producing the autograft, homograft or allograft serves as a scaffold and may be provided in the shape of the area to be treated. However, in other cases it may be advantageous that the autograft, homograft or allograft is provided in a non predetermined shape. For such case the inventors found that the provision as a suspension or a spray shows great advantages. The suspension or spray may also be provided without a biocompatible carrier. However, in one embodiment the suspension or spray comprises a biocompatible carrier as outlined below, wherein the biocompatible carrier consists of microscopic particles (microscopic biocompatible carrier) polymeric network. Microscopic means that the particles or biocompatible carrier have a thickness in the range of nanometer or micrometer.

In a preferred embodiment the biocompatible carrier provides a three-dimensional structure consisting of a network of fibres. Such structure provides a scaffold for the cells which facilitates the cultivation, correct morphology and functionality of the cells and furthermore increases the adherence of the cells to the carrier and enhances the facilitated functionality of the graft. The inventors found that such network of fibres serves as an efficient environment for the melanocytes and enhances their melanotic properties. Such properties can be measured by the activity of Dopa-tautomerase and/or melanin production of the cells. The inventors unexpectedly found that these properties are enhanced by the use of a biocompatible carrier according to the present invention. There is a variety of materials providing meshes, or networks, whose fibres protrude in all directions, enabling the cells to interface the fibres. Furthermore, the fibres should have a size/thickness that allows the cells to adhere to them. The inventors furthermore found that cells cultivated on such biocompatible carrier form a three-dimensional morphology within these meshes, whereas on the flat surfaces in cell culture only two-dimensional networks of cells are formed. It will be acknowledged by the person skilled in the art that the three-dimensional structure shall allow the melanocytes to migrate through the meshes formed by the network of the fibres and populate the entire scaffold. For example Loth, T. (Electrospinning als Methode zur Herstellung von fibrillären Zellträgern aus bioabbaubaren Polymeren, 2009), provides for such method of scaffold production. In a preferred embodiment of the invention the biocompatible carrier consists of at least one of the materials selected from the group consisting of polycaprolactone (PCL), collagen, human collagen I, human collagen IV, human collagen V, shortened and chemically cross-linked or otherwise modified collagen chains, fibrin, gelatine, and epidermis-equivalent keratinocyte-based carriers. Biocompatible carriers comprising keratinocytes are known by those skilled in the art and are commercially available. In one embodiment of the present invention the biocompatible carrier comprising keratinocytes is an Epidex® keratinocyte-based epidermal sheath (Euroderm Biotech & Aesthetics, Germany). In a particularly preferred embodiment the biocompatible carrier consists of polycaprolactone (PCL). Methods to produce such biocompatible carrier are known by those skilled in the art.

In one embodiment the melanocytes according to the present invention are provided in a suspension with collagen and fibrin.

It may be desirable that the autograft, homograft or allograft derivable by the methods according to the present invention is applied through different grafting application routes, such as suspension, aerosol, solid grafts as epidermal equivalent (using a solid biocompatible carrier as a scaffold). The properties of the autograft, homograft or allograft for the different routes may be adapted through the properties of the biocompatible carrier. Hence, the biocompatible carrier may be provided in different forms. The biocompatible carrier may be for example provided in a macroscopic form, such as a solid biocompatible carrier as a scaffold, e.g. in a shape fitting to the area to which the homo- or allograft shall be provided. Autograft, homograft or allograft can be provided as a suspension and/or aerosol, i.e. it can be applied as such on the area to be treated or be used as a spray. Hence, in one embodiment of the present invention the biocompatible carrier is provided as a macroscopic matrix for the autograft, homograft or allograft to be produced. In another embodiment the biocompatible carrier is provided as suspension and/or spray.

The resulting autograft, homograft or allograft may also be prepared for stocking until used for treatment of the disease. Hence, the method for producing the autograft, homograft or allograft according to the present invention may further comprise the application of suited buffers and/or media. The skilled artisan will recognize that the resulting autograft, homograft or allograft may be provided in different forms mostly depending on the form of the biocompatible carrier used in the method, supra.

The skilled person is able to adapt the period for cultivation of the melanocytes in the method for producing an autograft, homograft or allograft according to the present invention. The inventors found that the cultivation of the melanocytes under the conditions that enable the formation of a stratum basale drastically enhances the treatment potential of the autograft, homograft or allograft by enabling a correct morphology and cellular interactions, same as in epidermis. Hence, in one embodiment of the present invention the melanocytes are cultivated in the method for producing an autograft, homograft or allograft according to the present invention in order to anatomically simulate formation of a stratum basale.

The skilled artisan knows how to determine whether the melanocytes form a stratum basale The stratum basale is a basal layer of the epidermis, where the melanocytes reside. The epidermis is composed of 4-5 layers depending on the region of skin being considered. Those layers in ascending order are the basal/germinal layer (stratum basale/germinativum), spinous layer (stratum spinosum), granular layer (stratum granulosum), clear/translucent layer (stratum lucidum), and cornified layer (stratum corneum). The keratinocytes represent the majority of the cells in the upper four layers. Therefore the keratinocytes in culture can be stratified in order to mimick epidermal anatomy (so called epidermal equivalents). The inventors found that the provision of the autograft, homograft or allograft that corresponds to epidermal anatomy preserves the functionality of melanocytes and provides a potential for eventual treatment of depigmentation diseases.

The inventors furthermore found that the cultivation of the keratinocytes until the formation of a stratum corneum drastically enhances the treatment results of the autograft, homograft or allograft. Hence in one embodiment of the present invention the keratinocytes are cultivated in a medium-air interface until formation of a stratum corneum prior to stratification of the method for producing an autograft, homograft or allograft according to the present invention. Stratum corneum is the upper stratum of the epidermis. It consists of flattened keratinized keratinocytes. It can be morphologically determined in the cross sections of the stratified epidermal equivalents that the upper stratum is keratinized. Also, a possibility of staining keratinized cells to corroborate the morphological analysis exists. The person skilled in the arts, hence, is able to determine when the keratinocytes have formed a stratum corneum. However, in a preferred embodiment of the method for producing autografts, homografts or allografts according to the present invention the keratinocytes are cultivated for 8 to 20 days, preferably for 10 to 15 days, even more preferably for 11 to 12 days. In a preferred embodiment the keratinocytes are cultivated at a medium-air interface.

Medium and conditions for cultivation of keratinocytes are known by the skilled person. A suited cultivation methodology, e.g. medium and conditions, is disclosed in Int Wound J. 2009 June; 6(3):226-32.

The inventors unexpectedly found that a ratio of keratinocytes to melanocytes of 10:1 increases the efficacy of the autograft, homograft or allograft, by maintaining melanocyte functions and cellular interactions similarly to that in epidermis, and hereby prospects of the eventual treatment of diseases as outlined herein below. Hence, in one embodiment of the method for producing an autograft, homograft or allograft according to the present invention, the keratinocytes are stratified on top of the cultivated melanocytes in a ratio of 10:1.

The cultivation in step of the method for producing an autograft, homograft or allograft should be performed in order to cultivate both, melanocytes and keratinocytes. In one embodiment the cultivation step is performed in a neutral cultivation medium. A "neutral medium" in context with the present invention relates to a medium that does not contain supplements that affect melanocytes or keratinocytes. Hence, in one embodiment of the present invention the neutral cultivation medium does not comprise a growth factor selected from the group consisting of β-adrenergic receptor ligands, such as epinephrine and derivatives thereof, and/or $Ca^{2+}$ and/or Vitamin C and/or EGF and/or bFGF/FGF2 and/or Endothelin-1, α-MSH, SCF and/or NGF-β and/or HGF and/or Gentamycin, epidermal growth factor, hydrocortisone, cholera toxin, adenine, triiodothyronine, and alpha-MSH. In a further embodiment the neutral cultivation medium comprises one or more components selected from the group consisting of medium base, preferably DLM base or DMEM base, fibroblast growth factor, N6-2'-dibutyryl adenosine-3'-5'-cyclic monophosphate (db-AMP), L-glutamine, 0.5% to 20% serum, preferably 0.5% of foetal serum or 10% or less human serum.

In a preferred embodiment the cultivation step(s) of the method for producing an autograft, homograft or allograft is performed under hypoxic conditions; or normoxic conditions.

Furthermore, in one embodiment the cultivation may be performed as a medium-air interface or as a medium-covered epidermal equivalent.

The method for producing an autograft, homograft or allograft in a preferred embodiment is performed under the following conditions: $O_2$ content of approximately 5%, $CO_2$ content of approximately 5%, and a temperature of 37° C. (as revealed in Dieckmann et al, Exp Dermatol. 2010 June; 19(6):543-5).

The skilled artisan knows methods for performing cultivation and/or incubation of cells. For example the cells may be covered with the medium or the cells may be present at the medium-air interface. In one embodiment of the present invention the biocompatible carrier is located at the medium-air interface, i.e. the biocompatible carrier is in contact with the medium at its lower side and in contact with the air at its upper side. In another embodiment of the invention the biocompatible carrier with cells is covered with the medium, i.e. not in contact with the air.

In a further preferred embodiment the incubation step of the method for producing an autograft, homograft or allograft is performed under normoxic conditions, wherein the biocompatible carrier is covered with the incubation medium. In another embodiment, the incubation step of the method for producing an autograft, homograft or allograft is performed under normoxic conditions, wherein the biocompatible carrier is at the medium/air interface. In yet another embodiment, the incubation step of the method for producing an autograft, homograft or allograft is performed under hypoxic conditions, wherein the biocompatible carrier is at the medium/air interface. In yet another embodiment, the incubation step of the method for producing an autograft, homograft or allograft is performed under hypoxic conditions, wherein the biocompatible carrier is covered with the incubation medium.

The incubation step of the method for producing an autograft, homograft or allograft is performed until the desired properties are reached. These include the biomechanical stability, i.e. the resulting biocompatible carrier covered with keratinocytes and melanocytes shall provide a rigidity that allows the application of the derived autograft, homograft or allograft to the target region without the collapsing of the autograft, homograft or allograft. Furthermore, cross sections along with staining of melanin, tyrosinase, gp100 variants, should show presence of melanocytes at the lower phase of the graft, which is the anatomic equivalent of the stratum basale. Melanocytes stretch their dendrites into the upper phase, composed of keratinocytes (anatomically equivalent to the upper strata—spinous layer (stratum spinosum), granular layer (stratum granulosum), clear/translucent layer (stratum lucidum), and cornified layer (stratum corneum). Each melanocyte interfaces with up to 40 keratinocytes, forming so-called epidermal units. Cell soma and the dendrites of melanocytes should contain visible melanosomes of type I-IV, especially at the points of interface with the keratinocytes. Melanosomes are delivery packages—vesicles that serve for secretion of melanine. Melanosomes contain melanine and also various isoforms of glycoprotein 100 (gp100), therefore they may be observed by staining of gp100 proteins (for example, HMB45 and NKI-beteb variants).

In a preferred embodiment the incubation step of the method for producing an autograft, homograft or allograft is performed for 1 to 10 days, preferably 2 to 3 days.

The skilled artisan furthermore is aware of the fact that the incubation temperature has to be adapted to the needs of the cells. All the incubations within the present invention are performed at a temperature of approximately 20° to 37° C., preferably all the incubation steps of the methods disclosed herein are performed at 37° C.

The inventors found that an autograft, homograft or allograft according to the present invention and/or melanocytes according to the present invention can be used for the treatment of depigmentation of the skin. Hence, the present invention also relates to an autograft, homograft or allograft according to the present invention and/or melanocytes according to the present invention for use in treating a disease, preferably for use in treating scars and/or for use in treating a disease selected from the group of leukoderma, vitiligo, quadrichrome vitiligo, vitiligo ponctué, syndromic Albinism, such as Alezzandrini syndrome, Hermansky-Pudlak syndrome, Chédiak-Higashi syndrome, Griscelli syndrome (Elejalde syndrome, Griscelli syndrome type 2 and Griscelli syndrome type 3), Waardenburg syndrome, Tietz syndrome, Cross-McKusick-Breen syndrome, ABCD syndrome, Albinism-deafness syndrome and Vogt-Koyanagi-Harada syndrome, oculocutaneous albinism, hypomelanosis (idiopathic guttate hypomelanosis, phylloid hypomelanosis, progressive macular hypomelanosis), piebaldism, nevus depigmentosus, post-inflammatory hypopigmentation, pityriasis alba, Vagabond's leukomelanoderma, Yemenite deaf-blind hypopigmentation syndrome, Wende-Bauckus syndrome, Woronoff's ring, amelanism, Leucism, and diseases associated with depigmentation of the skin.

In one embodiment the present invention relates to an autograft, homograft or allograft derivable by a method for producing an autograft, homograft or allograft according to the present invention for use in treatment of a disease. In a preferred embodiment, the present invention also relates to an autograft, homograft or allograft according to the present invention and/or melanocytes according to the present invention for use in the treatment of scars and/or the treatment of a disease selected from the group of leukoderma, vitiligo, syndromic Albinism piebaldism, nevus depigmentosus, postinflammatory hypopigmentation, and diseases associated with depigmentation of the skin.

The autografts, homografts or allografts may be applied directly onto the depigmented skin area or scars. However, the area to be treated may in one embodiment be pretreated. In a preferred embodiment the skin area to be treated according to the present invention is pre-treated by dermabrasion of an epidermal layer corresponding to the thickness of the graft, preferably by using erbium:YAG Laser.

In a preferred embodiment the autograft, homograft or allograft derivable by a method for producing an autograft, homograft or allograft according to the present invention for use in treating a disease the autograft, homograft or allograft is applied to the area to be treated as a suspension or a spray. In another embodiment the autograft, homograft or allograft is applied to the area to be treated as a solid autograft, homograft or allograft. In a preferred embodiment the autograft, homograft or allograft is applied on the area to be treated after dermabrasion as outlined above. In a one embodiment of the present invention the autograft, homograft or allograft comprises separated melanocytes obtainable by a method according to the present invention.

The application of the autograft, homograft or allograft may be performed in different ways. For example if a solid autograft, homograft or allograft is used, the autograft, homograft or allograft may be directly applied on the area to be treated. However, as outlined above the autograft, homograft or allograft in one embodiment of the present invention is a suspension or spray. In such case the autograft, homograft or allograft is applied as a suspension onto the area to be treated or sprayed thereon, respectively.

In one embodiment melanocytes and keratinocytes are applied onto the area to be treated. If this is performed with suspensions or sprays with separated melanocytes and keratinocytes it may be performed in different orders. For example a suspension or spray comprising melanocytes according to the present invention may be mixed with a suspension comprising keratinocytes as outlined herein and then be applied together as a suspension or a spray. In another embodiment a suspension comprising melanocytes according to the present invention is applied on the area to be treated as a suspension or as a spray and then a suspension comprising keratinocytes as outlined herein is applied on said area as a suspension or a spray. The spray may further comprise fibroblasts and keratinocytes as outlined above.

In one embodiment of the present invention the area to be treated is sealed after application of the respective suspension or solid autografts, homografts or allografts.

The area treated as outlined herein is in one embodiment left unstimulated after treatment to recover and gain own pigmentation. In a further embodiment the area is stimulated with UV light using suberythematogenous doses of 311 nm UVB 2-3 times weekly, as described previously (Dermatology. 2009; 218(4):342-3).

The autograft, homograft or allograft and/or melanocytes according to the present invention can also be used for aesthetic purposes, for example, in cosmetics. Accordingly, a cosmetic composition comprising the autograft, homograft or allograft and/or melanocyte(s) according to the present invention is provided. Likewise, the present invention relates to a method for the cosmetic treatment comprising treating an individual or subject with an autograft, homograft or allograft and/or melanocytes as provided herein.

The following non-limiting examples and figures illustrate the invention:

EXAMPLES

The following examples are included to demonstrate preferred embodiments of the invention. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Cultivation, Expansion, Differentiation, Selection of Pure Melanocyte Culture
Experimental Design and Methods
Hair Biopsy To begin the procedure of extracting the melanocytes from hair roots, one needs to pluck 30 to 80 anagen hairs from the temporal region of the scalp. The biopsy is painless, scarless and requires less hairs than one spontaneously looses on daily basis. Up to five hairs of the temporal area are held close to the root with a disinfected forceps and pulled in the direction of the hair growth. The hairs were stored in Phosphate Buffer Saline (PBS, without Calcium addition until preparation.
Selection of the ORS Mid Part, Preparation The long part of the hair shaft was cut off and a short part of the shaft was left for handling purposes. The hair roots were shortened from the proximal end by cutting the hair bulb off (FIG. 1). As the bulb usually yields over 90% fibroblasts in our experience, a significant part of cellular contaminants is avoided by removing this portion.

The hairs were serially washed five times for one minute in separate 50 μg/ml Gentamycine (Ratiopharm) and 10 μg/ml Amphotericin (Amimed) in Dulbecco's Modified Eagle Medium (DMEM) and subsequently washed with PBS.
Loosening of Extracellular Matrix Extracellular matrix was loosened by digestion with solution of Collagenase V (Sigma-Aldrich) in Phosphate Buffer Saline (PBS), 5 mg/ml, at 37° C. for 10 mM.
Media The hair follicles and ORS cells were cultivated in DermaLife Melanocyte medium (Life Line Cell Technology, Walkersville, Md., USA), DLM medium base of low bovine serum content (0.5%), L-Glutamine (6 mM), Insulin (5 ng/ml), Vitamin C (50 ng/ml), Epinephrine (1 nM), StiMel factor cocktail (1%) and Gentamycine (50 ng/ml), according to the manufacturers specifications. The medium did not contain cholera toxin nor any tumour promoters such as phorbol-12-myristate 13-acetate (PMA, TPA).
Medium-Air Interface Cultivation Conditions The shortened hair roots were placed on 24 mm Transwell® nylon-meshes with 0.4 μm Pore Polyester Membrane Insert (Corning) and grown in medium-air-interface conditions. Nutrition was supplemented by 1 ml DLM medium (DermaLife), the amount sufficient to enable contact with the mesh and the cells from underneath, hereby supplying the necessary nutrients. The upper parts of the follicles were exposed to hypoxic gas mixture, 5% $O_2$, 5% $CO_2$ and 90% $N_2$. The hair roots were allowed to expand for 2 weeks and were then covered with DLM medium. This period is usually sufficient to reach up to 40% confluence on the mesh (FIG. 1 e).
Adherent Culture Cells were further cultivated in DLM medium until they reached over 90% confluence. They were then trypsinized, harvested and taken into an advanced primary culture. The obtained outer root sheath cells were seeded on an adherent surface of the 10 cm² wells culture dishes (Corning) in the third week of cultivation (day 18±2). The start of the culture at the adherent surface was marked as start passage (p0).

Differential Trypsinization

The cells were further differentially trypsinized upon reaching 80% confluence at the uncoated adherent surface. After 4 minutes of 0.04% Trypsin/0.03% EDTA incubation at room temperature, detached melanocytes were collected and passaged into the T25 cell culture flasks. The rest of the cells, keratinocytes and fibroblasts, remained adherent and they were not transferred into the next passage of the culture. Differential trypsinization was performed at every passage as routine measure of culture maintenance.

Geneticin Treatment

Growth of keratinocytes and fibroblasts in later stages of differentiation was foremost prevented by treating the whole culture with Geneticin (50 µg/ml) for 48 h at day 22±2 of differentiation. The effect of Geneticin is to block translation in all cells, hereby affecting primarily the quickly dividing cells, e.g. keratinocytes and fibroblasts. The metabolism and division of melanocytes in the culture is slow, therefore they remained unaffected by short treatment with Geneticin (FIG. 2, F-H).

The advanced primary culture of ORS cells was maintained in DermaLife Melanocyte medium (Life Line Cell Technology, Walkersville, Md., USA), DLM medium base of low bovine serum content (0.5%), L-Glutamine (6 mM), insulin (5 µg/ml), vitamin C (50 µg/ml), epinephrine (1 µM), StiMel factor cocktail (1%) and gentamycine (50 µg/ml). The medium did not contain cholera toxin nor any tumor promoters such as phorbol 12-myristat 13-acetate (PMA, TPA)

Control Cells

Epidermal melanocytes (normal human epidermal melanocytes, NHEM, PromoCell) were cultivated in the Melanocyte M2 Basal Medium supplemented with M2 Supplement Mix (Promocell) upon the manufacturers guidelines, at 37° C., under normoxic conditions. The cells were used as fully differentiated control cells.

Fibroblasts used as non-melanotic control were cultivated in DMEM, supplemented with 10% bovine serum, 2 mM L-Glutamine, and 100 U/ml penicillin, as well as 0.1 mg/ml streptomycin.

Production of the Biocompatible Carrier (PCL Scaffolds)

The biocompatible carrier (in this case a scaffold consisting of PCL; referred to as PCL scaffolds) were produced by the standard electrospinning procedure, as revealed in Loth, T., Electrospinning als Methode zur Herstellung von fibrillären Zellträgern aus bioabbaubaren Polymeren. 2009.

Polycaprolacton (PCL)-Fiber Meshes originate in electrospinning process that creates a network of fibers by subjecting a jet of polycaprolactone solution to high voltage. Polimer solution is prepared from the PCL powder solved in Chloroform (CHCl3):Methanol (MetOH) (7:1) agitated for 1 h. The solution was placed in a syringe with a blunt-end needle and mounted onto a syringe pump (KD Scientific Inc., USA). DC current was connected to both the syringe needle and grounded collector glass plate, forming a closed circuit. This creates an electric field between the PCl polymer solution and the glass collector plate and leads to the formation of a continuous jet between a maintained droplet at the top of the needle and the glass collector plate. As the jet strikes against the glass plate, it assumes the future network formation. Solution of chloroform and methanol evaporates quickly, and the PCL fibre remains in the mesh. The mesh is withdrawn from the glass by 100% ethanol. Finally, the fibre mesh is dried out using an exicator device coupled to a membrane vacuum pump (VP 820; VWR International GmbH, Deutschland).

By combining the parameters of electrospinning procedure, varying fibre thickness, fibre orientation and mesh thickness can be obtained. In this application, two basic parameter sets were used to form 100 µm thick meshes networked from 'thin' and 'thick' fiber. 'Thin' fibre mesh (2-3 µm diameter) were obtained by using 14% PCL at flow-rate 2 ml/h, with the electrode 18.5 cm apart from the collector electrode, using a 22 Gauge needle to generate the jet from a 0.4-0.5 ml droplet. 'Thick' fibre mesh (8-10 µm diameter) were obtained by using 20% PCL at flow-rate 10 ml/h, with the electrode 30 cm apart from the collector electrode, using a 14 Gauge needle to generate the jet from a 0.4 to 0.5 ml droplet.

The structure, fibre orientation and fibre thickness were analyzed and quantified by the means of light microscopy (Nikon Eclipse TE 2000-S; Nikon Corporation/Instruments, Deutschland), and electron microscopy (Raster electron microscope CS 44; CamScan; Obducat CamScan Ltd, UK).

The scaffolds were circle-shaped with a sterile hollow punch, with an 8 mm diameter so that they covered the 10.7 mm wide bottom of the 96-well plate in calibrated condition. They were sterilized with 75% ethanol for 30 min, washed with PBS five times. Before the cells were seeded onto the scaffolds, the material was calibrated in the DLM medium or PC-1 medium for 24 hours.

The cells were seeded onto the scaffolds, 10.000 cells pro scaffold, suspended in 200 µl medium.

Characterization of Cell Types

The cells were characterized by their morphology, expression of marker proteins Tyrosinase, variants of gp100 protein (melanosome marker)—NKI-beteb and HMB45, activity of DOPA-tautomerase, and reaction to IBMX and melanin content.

In agreement with the literature data several cell types were determined based on morphology: small round cells, small spindle-like cells, cells with characteristic fibroblast morphology and cells with pebble-like keratinocyte morphology, tri- or multidendritic cells with melanocyte morphology (Tobin D J, Colen S R, Bystryn J C. J Invest Dermatol 1995: 104: 86-89; Dieckmann C, Milkova L, Hunziker T, Emmendörffer A, Simon J C. Human melanocytes can be isolated, propagated and expanded from plucked anagen hair follicles. Exp Dermatol. 2010 June; 19(6):543-5; Zhu W Y, Zhang R Z, Ma H J, Wang D G. Pigment Cell Res. 2004 December; 17(6):668-73. Isolation and culture of amelanotic melanocytes from human hair follicles; Bosserhoff A K, Ellmann L, Kuphal S. Melanoblasts in culture as an in vitro system to determine molecular changes in melanoma. Exp Dermatol. 2011 May; 20(5):435-40).

The melanocytes were characterized based on morphological criteria for melanocytes reported by Bosserhoff et al. The set of criteria used in this study in terms of melanotic features, proliferation and attachment helped us discriminate the derived Human melanocytes HM cells, abbreviated from Hair follicle-derived Melanocytes from melanocyte precursors. Obtained cells in the end culture were melanotic, proliferated at comparable pace as NHEM epidermal melanocytes and weakly adhered to the surfaces of cell culture vessel, unlike the amelanotic, quickly dividing and strongly adherent precursors reported by Bosserhoff.

Morphological criteria for melanocytes were combined with the expression of marker proteins: Tyrosinase (FIG. 3e) and variants of gp100 protein (melanosome marker)—NKI-beteb (FIG. 3d) and HMB45 (FIG. 3f). Furthermore, reaction to 3-isobutyl-1-methylxanthine (IBMX) (FIG. 12 f, 12 h), activity of Tyrosinase, Dopachrome-tautomerase/Tyrosinase-related protein 2 (DCT/TRP-2) was tested as well as the DHIC-oxidase/Tyrosinase-related protein 1 activity (TRP-1) in the L-DOPA conversion test (FIG. 12 e, 12 g). Moreover, melanin content was determined at 13.7 pg/cell in unstimulated HM cells and at 22.6 pg/cell after converting L-DOPA into melanin.

Expression of CD90 was used as a criterion for undifferentiated cells, by rule fibroblasts (positive CD90 signal, FIG. 12c), and as exclusion factor for differentiated melanocytes (absence of CD-90 signal, FIG. 12d).

Immunofluorescence

Melanocytes

The cells grown in chamber slides coated with gelatine were washed with PBS and fixed with ice-cold Para formaldehyde (PFA, 4%) for 8 minutes, then washed with PBS again. The cells were blocked with 0.5 ml of 2% bovine serum albumin and permeabilised with 0.1% Triton-PBS solution for 1 h. Solutions of primary mouse-generated antibodies against NKI\beteb Tyrosinase and HMB-45 (Abcam) were set at 2% in PBS with 2% BSA/0.1% Triton and incubated with the cells on scaffolds overnight at 4° C. After washing with 2% BSA/0.1% Triton solution, biotinylated anti-mouse secondary antibody was added to the cells and incubated for 1 h, then washed. Solution of 2% BSA-PBS/0.1% Triton/0.25% IGG was incubated with the cells for one hour, then washed. Finally, Streptavidine-coupled Alexa594® and Alexa 488® fluorochrome 0.25% solution in 2% BSA/0.1% Triton were incubated with the cells together with 1/1000 DAPI nuclear dye for 1 h, then washed two times with 2% BSA/0.1% Triton solution. Cells were fixed onto glass with Fluoromount® sealing liquid and covered with a glass slip.

The marker signals were analysed by means of fluorescence microscopy (Nikon Eclipse Ti-S; Nikon Corporation, Deutschland). The cellular and nuclear signals were counted by means of ImageJ 1.42q NIH public software.

Grafts

The cells on scaffolds were washed with PBS and fixed with ice-cold Para formaldehyde (PFA, 4%) for 8 minutes, then washed with PBS again. The cells were blocked with 0.5 ml of 2% bovine serum albumin 2% BSA-PBS and permeabilised with 0.1% Triton-PBS solution for 1 h. Solutions of primary mouse-generated antibodies against NKI\beteb and Tyrosinase were set at 2% in PBS with 2% BSA/0.1% Triton and incubated with the cells on scaffolds overnight at 4° C. After washing with 2% BSA/0.1% Triton solution, biotinilised antimouse secondary antibody was added to the cells and incubated for 1 h, then washed. Solution of 2% BSA-PBS/0.1% Triton/0.25% IGG was incubated with the cells for one hour, then washed. Finally, Streptavidine-coupled Alexa594® (red) and Alexa 488® (green) fluorochrome 0.25% solution in 2% BSA/0.1% Triton were incubated with the cells together with 1/1000 DAPI nuclear dye, for 1 h, then washed two times with 2% BSA/0.1% Triton solution. Scaffolds with the cells were left to dry out for 2 min and fixed onto glass with Fluoromount® sealing liquid and covered with a glass slip.

The marker signals were analysed by means of fluorescence microscopy (Nikon Eclipse Ti-S; Nikon Corporation, Deutschland) and Laser-Scanning microscope (LSM 510 Meta, Carl Zeiss Jena GmbH, Deutschland).

L-Dopa Tautomerase Activity

Change of colour due to the build-up of melanin upon L-DOPA tautomerization and subsequent oxidation was visually registered. The cells, together with the scaffolds were submitted to a five-fold freeze/thaw procedure on dry ice/37° C. water bath in order to disrupt the cell membranes. The lysates were centrifuged at 4° C. at 14000 rpm for 30 min. The supernatant was used to test the Tyrosinase, TRP-1 and TRP-2 enzymes activity. The lysate (100 µl) was incubated with 200 µl of L-DOPA solution (10 mg/ml) for 6 h. The extinction at 475 nm was measured by the means of Multiscan® Spectrum (Thermo Fisher Scientific Germany Ltd. & Co. KG, Deutschland) Elisa plate reader in order to determine the exact amount of the melanin produced. The presence of melanin synthetized from L-DOPA substrate confirmed the activity of Tyrosinase, DOPA-tautomerase/Tyrosinase-related Protein 2 (TRP-2) and DHIC-oxidase/Tyrosinase-related Protein 1 (TRP-1).

IBMX Induction

The HM cells were incubated with 20 mg/ml 3-isobutyl-1-methylxanthine (IBMX) for 7 days and then analyzed for melanin content against untreated HMs, as described earlier on in this application.

Melanin Content

Cells

The cells were trypsinized, counted or adjusted to total of 10000 cells and treated with 150 µl of 1M NaOH and washed several times with a pipette, then pelleted by centrifugation at 14000 rpm for 30 min, 4° C. The cell pellet was incubated at 37° C. for 6 hours in 1M NaOH. The amount of 150 µl of the resulting cell lysate was transferred to a flat-bottom 96-well plate, filled up with 1M NaOH lysing solution until 300 µl end volume and the extinction at 475 nm was measured by means of a plate reader in order to quantify the melanin concentration and subsequently its total content in the measured sample. Content of melanin was adjusted to amount per cell.

Synthetic melanin was used as solution for the standard curve. Melanin solution of 100 µg/ml was incubated in 1M NaOH for 5 hours at 60° C. and serial dilutions were prepared (100; 50; 25; 12.5; 6.25; 3.125 µg/ml), measured for extinction at 475 nm and used for concentration comparison.

Graft

The cells together with PCL scaffolds were treated with 150 µl of 1M NaOH and washed manifold with a pipette. Scaffold was subsequently withdrawn. The cell pellet was incubated at 37° C. for 6 hours. 150 µl of the cell lysate was transferred to a flat-bottom 96-well plate, filled up with 300 µl lysate solution and the extinction at 475 nm was measured with a plate reader in order to quantify the melanin content.

Synthetic melanin was used as solution for the standard curve. Melanin solution 100 µg/ml was incubated in 1M NaOH for 5 hours at 60° C. and serial dilutions were prepared (100; 50; 25; 12.5; 6.25; 3.125 µg/ml), measured for extinction at 475 nm and used for concentration comparison.

Incorporation into Epidermal Equivalents

Melanocytes and keratinocytes were cultivated from ORS of the hair follicle, melanocytes as described in this application and keratinocytes as described in Cells Tissues Organs 2002; 172:79-85. Melanocytes were seeded on the 24 mm Transwell® nylon-meshes with 0.4 µm Pore Polyester Membrane Insert (Corning). Upon a 4 h adhesion, suspension keratinocytes in 9-fold suffix were added and allowed to stratify over 11 days in the DermaLife Keratinocyte medium (Life Line Cell Technology, Walkersville, Md., USA), or DMEM/F12 (3:1) supplemented with 10% human serum, 20 ng/ml epidermal growth factor, hydrocortisone, cholera toxin 10 ng/ml, adenine and triiodothyronine. The stratified construct represents an epidermal equivalent which mimics epidermal anatomy. Melanocytes reside in stratum basale and the keratinocytes are the constituents of the upper layers. At day 12, the upper keratinocyte stratum should be equivalent to stratum corneum, morphologically identifiable by flattened cells.

The epidermal equivalents were cross-sectioned by the means of cryotome into 200 μm slices, fixed, dyed using the described immunofluorescence procedure and analysed by fluorescent microscope. Additionally, slices were dyed with Nile Blue in order to mark the cells and their subsections with melanin content.

Data Validation

All experiments were performed using material of four donors in five biological experiments, set up in three technical replicas. The data were validated for statistical significance of the intertreatment differences by the means of two-tailed Student's t-test.

Comparative Data

We have additionally compared the method of Dieckmann et al. (Exp Dermatol. 2010 June; 19(6):543-5. Epub 2010 Mar. 30) to the method according to the present Mention, using this similar experimental platform to cultivate HM melanocytes from hair samples. We have followed both cultivation and differentiation procedures synchroniously. At the point of Geneticin selection, we have synchroniously treated all the cells in order to examine the fibroblast and keratinocyte content of the both preparations at that stage.

Results

Cultivation, Expansion, Differentiation, Selection of Pure Melanocyte Culture

The procedure has yielded a higher expanded culture of 95-100% pure, almost fully differentiated human melanocytes, which reached the melanotic stage within 3 to 4 weeks post-biopsy, as early as p3 or p4 of the primary culture (FIG. 1-5). In particular, the cultivation and differentiating procedure from 60 hair follicles yielded $10^6$ pure, differentiated human melanocytes which reached melanotic stage within 3-4 weeks postepilation, in the third to fifth passage of adherent culture.

In comparison to the results of Dieckman et al., the method presented here reached an output of $10^6$ HM in half the time. Further on, the difference between methods was obvious already at the point of harvesting the cells from the Transwell nylon meshes in order to take them into adherent culture; the number of harvested cells exceeded that of the Dieckmann method (loc. cit.) by factor 2.46. Further on, the portion of fibroblasts and keratinocytes in the harvested material was much higher according to the Dieckmann method (loc. cit.), since most of them died during the Geneticin selection and an extremely low number of cells remained after the Geneticin treatment. In contrast to the outcome of Geneticin selection of cells cultivated according to Dieckmann et al (loc. cit.), large number of cells cultivated as described herein survived this selection step and were able to give raise to $10^6$ HM in four weeks.

Figure 5:
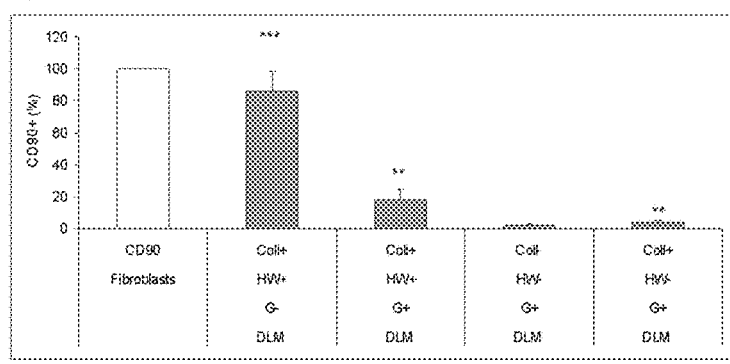
FIG. 5 is a graphical representation of the relative fibroblast contamination in an ORS melanocyte culture. The grey bars are showing the percentage of CD-90-positive cells in culture. Coll+/− corresponds to Collagenase V treatment, HW+ stands for presence of the bulb, HW− stands for absence of the bulb (The bulb has been severed from the rest of the root), G+/− stands for Geneticin treatment, DLM for DermaLife culture media applied. The white bar represents fibroblast control, grown in a separate culture, showing 100% of CD-90-expressing cells.

The uppermost purity was reached by synchroniously combining DLM medium, microdissection (severance of the proximal part of the follicle (bulb)), digestion by Collagenase, selection by Geneticin and differential trypsinization, yielding 96% melanocyte-marker-expressing cells (FIG. 4), with negligible residual content (2.39-4.2%) of CD-90-expressing cells (FIG. 5).

Combined microdissection, Collagenase and Geneticin treatment increased the purity of HM culture by 87.65% compared to cultures without treatments (FIG. 4) and lowered fibroblast content in HM culture by 82.12% (FIG. 5).

Geneticin treatment increased HM culture purity by 67.7% (FIG. 2d) and diminished fibroblast content by 68% (FIG. 5).

Collagenase treatment increased the purity of Geneticin-treated HM cultures by 12.72% (FIG. 5).

Excision of the proximal follicle part (microdissection) increased HM content by 20% when combined with subsequent Collagenase and Geneticin treatment (FIG. 4), lowering fibroblast presence by 14.15% (FIG. 5). All differences between treatments were statistically significant (p<0.05) to very highly significant (p<0.005) according to Student's t-test, except between DLM/−Col/−HF/+G (non-digested shortened follicles grown in DLM and selected with Geneticin) and other treatments. Culture purity of HM was maintained by cell passages using differential trypsinization, exposing adherent cell culture to Trypsin/EDTA solution for 4 minutes at room temperature and using the detached melanocytes in the supernatant for further cultivation (based on In Vitro. 1984 May; 20(5):447-50, Exp Cell Res. 1982 December; 142(2):309-15).

After the third passage of adherent cultivation, HM cells fully displayed features of differentiated melanocytes. The cells had a typically large tri-to-multidendritic soma (FIGS. 1d and 2h), expressed NKI-beteb, HMB45 and Tyrosinase (FIG. 2a-c), converted L-DOPA and synthesized melanin (FIGS. 12e and g). IBMX treatment induced dendrite growth and melanin synthesis in all cells (FIGS. 12 f and h).

Conclusions

The present invention provides an improved method for generating melanocytes comprising the microdissection of the epilated hair, the treatment with Collagenase and treatment with antibiotics, the differentiation in a differentiation medium as defined above. Further improvements were reached by maintenance of the obtained culture purity by differential trypsinization. This method leads to a higher yield, quicker differentiation of melanocytes and enhanced purity of HM culture when compared to the method disclosed in Dieckmann et al. (Dieckmann C, Milkova L, Hunziker T, Emmendörffer A, Simon J C. Human melanocytes can be isolated, propagated and expanded from plucked anagen hair follicles. Exp Dermatol. 2010 June; 19(6):543-5. Epub 2010 Mar. 30). The synergy of faster growth, higher yield, ample differentiation and out-selection of competing cells reduced the time necessary to cultivate $10^6$ HM by 50% compared to the method of Dieckmann (loc. cit.).

In the method according to the present invention the proximal fibroblast-rich part of the follicle was excised. Fibroblasts divide quickly, competitively out-selecting the slower-dividing melanocytes. By reducing the initial fibroblast content in culture, the nutritional and spatial competition is lowered.

Partial digestion of the follicle collagen by Collagenase V loosened the extracellular matrix and accelerated cell migration from the ORS pool.

Single short-term treatment by Geneticin efficiently removed keratinocytes and fibroblasts from the culture, leaving melanocytes unharmed.

Differential trypsinization increased and maintained HM purity. Melanocytes are weakly adherent and quickly retract dendrites upon short trypsinization, ending up in suspension early on and leaving adherent fibroblasts and keratinocytes behind. Negligible residually adherent melanocyte loss was compensated by high HM yield ($10^6$ cells within 3-4 weeks).

The ORS cell pool was amplified from minimal, non-invasively gained material into quickly, putatively developed melanocytes.

All of the above provides pure, defined and sterile HM culture and makes the improved method preferable in non-invasive HM cultivation for purposes of graft-based treatments.

The cell expansion was accelerated and the cell purity was increased by the means of the above described combined treatments. The cultures obtained by a complete combination of the treatments grew most quickly, reached the highest purity yielding a 96% of melanocyte-marker-expressing cells (FIG. 2), hereby showing the lowest presence of contaminant cells with a negligible residual content of contaminant CD-90-expressing cells (FIG. 5).

Similar results were obtained with material from all probands and biological experiments in terms of cell yield (at least 1 million cells in 4 weeks) and purity. No significant differences between probands and experiments have occurred in terms of purity/contamination. As for the yield, individual differences were observed in the time necessary to obtain at least 1 million of differentiated melanocytes. However in all probands, biological experiments and replicas, a minimal yield of one million differentiated melanocytes was always reached in four weeks or less.

Characterization

Characterization criteria were fulfilled at the third passage or later. Before the p3, the cells were still negative for certain characterization parameters for melanocytes.

The cells had a typically large soma and at least three dendrites (FIG. 1 D), they expressed Tyrosinase, NKI-beteb and HMB45 (FIG. 3, 7, 9), successfully converted L-DOPA and synthesized melanin (FIG. 10). All of the cells reacted to the IBMX test, being successfully induced into melanin synthesis and dendrite growth.

Integration into PCL Fibre Mesh

Figure 7:
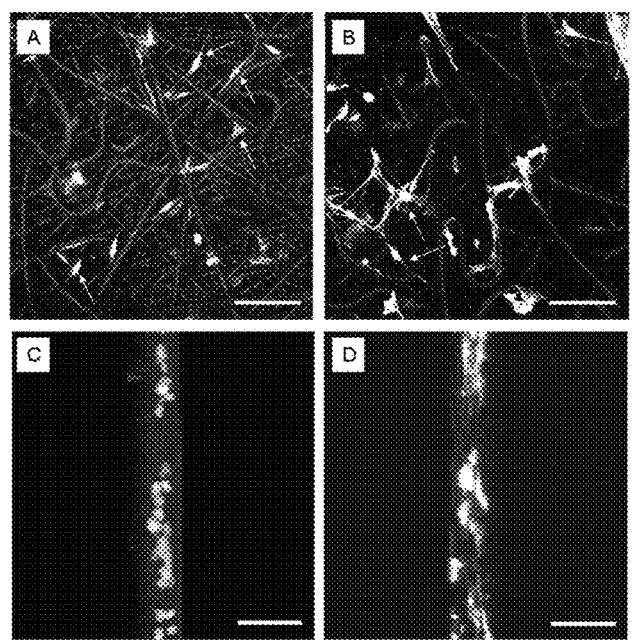
FIGS. 7A-7D are exemplary images of laser-scanning microscope capture of HM and NHEM on PCL Scaffolds. A: HM expressing Tyrosinase; B: NHEM expressing NKI\beteb; C: Side view of the ORS melanocyte-populated PCL-Scaffold; D: Side view of the epidermal melanocyte-populated PCL-Scaffold.
Figure 8:
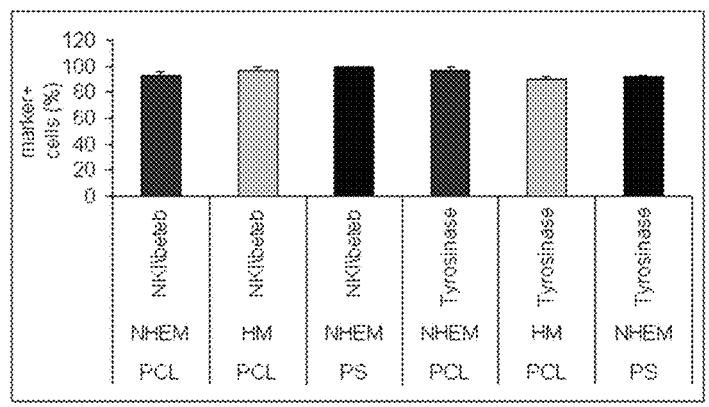
FIG. 8 is a graphical representation of melanocyte marker expression on PCL scaffolds and on a polystyrene adherent surface. The ratio of the number of nuclei against marker-positive cells is expressed as percentage.

The cells grown on PCL scaffolds were properly nested and assumed a typical morphology of melanocytes in the three-dimensional tissue context. They extended dendrites in multiple directions and interfaced the fibre of the scaffolds (FIGS. 7A and 7B). The cells migrated into the scaffolds and populated the entire depth of the network (FIG. 7C). The diffuse pattern of Tyrosinase and the localized pattern of gp100 variants were also typical for melanocytes (FIG. 7, 9). The gp100 variants were localized in melanosome vesicles near the dendrite interfaces (FIG. 9). Equally high percentage of cells, both in NHEM and HM, displayed gp100 variants and Tyrosinase on PCL scaffolds and on the polystyrene surface (FIG. 8).

Moreover, L-DOPA activity and melanin content of the cells on scaffolds were manifold higher than the cells on flat adherent polystyrene surfaces—roughly 6-7-fold in epidermal melanocytes and 2-fold in ORS melanocytes (FIG. 10).

Incorporation into Keratinocyte-Based Epidermal Equivalents

The epidermal NHEM were successfully incorporated into keratinocyte-based epidermal equivalents. They remained oriented towards the lower layer which corresponds to the stratum basale of human skin epidermis. The melanocytes maintained their characteristics and fully displayed the characterization parameters for melanocytes as described herein (FIG. 11).

Example 2

The Herein Provided Method is More Efficient in Producing Melanocytes Compared to the Method of Dieckmann (Loc. Cit.)

Materials and Methods

The method of Dieckmann et al. (Exp Dermatol. 2010 June; 19(6):543-5. Epub 2010 Mar. 30) was compared to the method according to the present invention, using this similar experimental platform to cultivate HM melanocytes from hair samples. We have followed both procedures synchroniously. The procedure of preparation, cultivation, differentiation and characterization according to the method described herein was conducted as described in Example 1. As described above, the herein provided method differs, inter alia from the method of Dieckmann by the use of an epilated hair, whereby the bulb of the hair has been removed, and by the incubation of the epilated hair with a collagen-degrading agent. In addition, the method of the present invention can comprise Geneticin treatment. The procedure of Dieckmann et al. (loc. cit.) was performed according to the given reference. The supplement for M2 as used in the method of Dieckmann (loc. cit.) contains Bovine Pituitary Extract 0.004 ml/ml, Basic Fibroblast Growth Factor (recombinant human) 1 ng/ml, Insulin (recombinant human) 5 mg/ml, Hydrocortisone 0.5 mg/ml, and Phorbol Myristate Acetate (PMA) 10 ng/ml. Cultivation conditions for the adherent culture according to Dieckmann (loc. cit.) involves medium Melanocyte Growth Medium M2, supplemented with SupplementMix, produced by Promocell, (Heidelberg, Germany). Because the SupplementMix of this medium contains PMA, which is a potent tumor promoter, the cells obtained by the method of Dieckmann (loc. cit.) are disadvantageous for therapeutical use.

At the point of Geneticin selection, we have synchroniously treated all the cells cultivated according to the present invention in order to selectively discard the fibroblast and keratinocyte content of the preparation at the stage of adherent culture as described herein. Further on, in order to clarify the role of the contaminant fibroblasts and keratinocytes as competitors against differentiating melanocytes, we have treated a separately set up experiment of the 'Dieckmann' (loc. cit.) cultivation, at the point of the initial passage of the adherent culture, with Geneticin.

The cells were stained with Trypsin blue and counted in Neubauer chamber at each passage.

Figure 13:
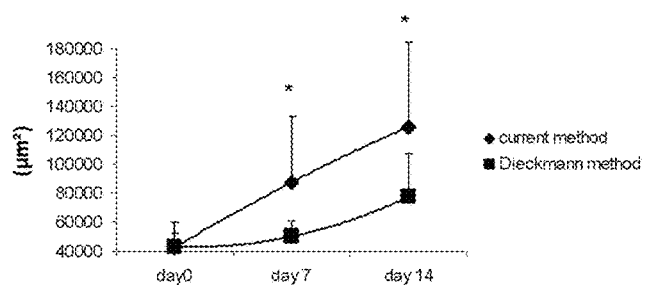
FIG. 13 is a graphical representation of the comparative changes of the Outer Root Sheath surface. Both the current method (♦) and the method of Dieckmann et al. (■) are depicted.

Measurement of the Outer Root Sheath Surface Changes:

Surface of the follicle ORS was measured by the means of Nikon NIS Elements BR (Version: 3.00) software. The ORS, which is morphologically clearly distinguishable, was selected from surface micrography of hair follicle by the means of an adjustable polygonal frame and the surface values were read out by software. The average values of ORS surface of four independently set up cultivation experiments with three technical replicates were compared at day 0, day 7 and day 14 (FIG. 13, 14).

Comparison of the Dieckmann (Loc. Cit.) Method and Herein Provided Method with Geneticin Addition:

Additionally, in order to withdraw the contaminant fibroblasts and keratinocytes as competitors against differentiating melanocytes, we have treated the 'Dieckmann' (loc. cit.) adherent culture with 50 µg/ml Geneticin after the p0 as a corresponding selection measure used in the current method.

Results
Cultivation, Expansion, Differentiation, Selection of Pure Melanocyte Culture The procedure has yielded a higher expanded culture of 95-100% pure, almost fully differentiated human melanocytes, which reached the melanotic stage within 3 to 4 weeks post-biopsy, as early as p3 or p4 of the primary culture (FIG. 1-5). In particular, the cultivation and differentiating procedure from 60 hair follicles yielded $10^6$ pure, differentiated human melanocytes which reached melanotic stage within 3-4 weeks postepilation, in the second to fifth passage of adherent culture. In comparison to the results of Dieckman et al., the method presented here reached an output of $10^6$ HM in half the time according to the published material and by far exceeded the yield of protocol by Dieckmann (loc. cit.) already in very early passages of adherent culture according to our findings.

ORS Surface Growth

Figure 14:
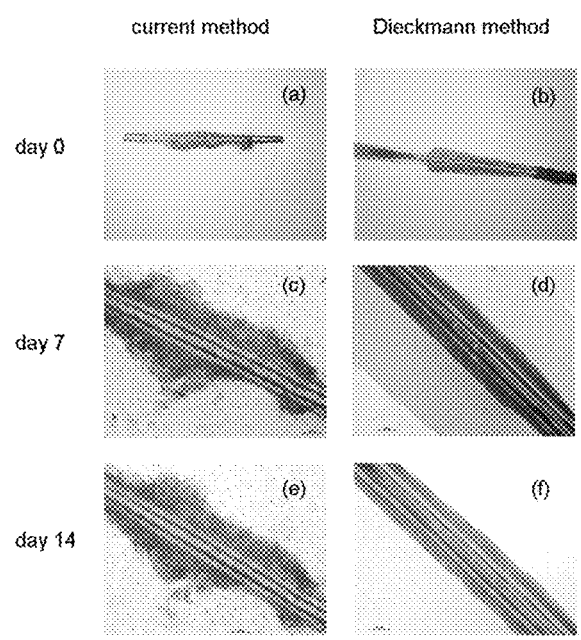
FIGS. 14A-14F are exemplary images of comparative ORS surface changes. A: Current method, day 0; B: Dieckmann method, day 0; C: Current method, day 7; D: Dieckmann method, day 7; E: Current method, day 14; F: Dieckmann method, day 14.
Figure 16:
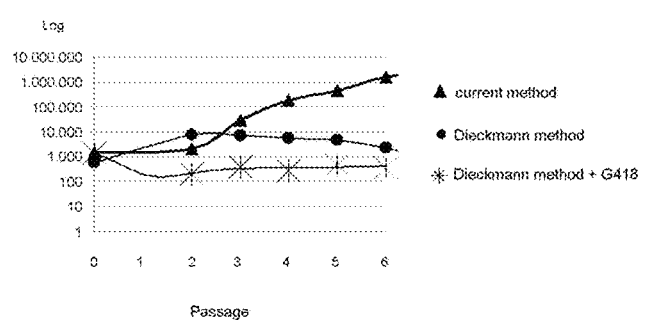
FIG. 16 is a graphical representation of the comparative growth in the adherent culture, per hair follicle. Growth curves of ORS cells per sampled hair follicle cultivated according to: (▲) the current method, (●) Dieckmann method, (*) Dieckmann method with Geneticin supplement during the first 6 passages of adherent culture. The graph is displayed logarithmically.

Difference in growth between methods was visible already on day 7 and day 14 of follicle cultivation on nylon meshes, with clearly displayed higher growth of the follicles cultivated upon the method described herein in comparison to the Dieckmann (loc. cit.) method (FIG. 14). The ORS surface of hair follicles digested with collagenase and cultivated according to the present invention, as described in Example 1, increased from 42.480±17.451 µm² on day 0 to 87.735±45.397 µm² on day 7 and 125.838±58.446 µm² on day 14, whereas the follicles cultivated according to the Dieckmann (loc. cit.) method increased from 43.302±9.226 µm² on day 0 to 50.039±10.753 µm² on day 7 and 77.488±29.569 µm² on day 14. The ratio of the Outer Root Sheath surface between the Dieckmann (loc. cit.) method and the current method hereby declined from 0.94 on day 0 to 0.69 on day 7 (p=0.01*) and 0.72 on day 14 (p=0.018*) (FIG. 13), displaying faster growth and migration of cells from collagenised follicles. At the point of harvesting the cells from the Transwell nylon meshes in order to take them into adherent culture, the number of harvested cells exceeded that of the Dieckmann (loc. cit.) method by factor 1.84 when all the sampled hair follicles were taken into account. (FIG. 16).

Comparative Growth in Adherent Culture

The cells in the adherent culture, cultivated according to the method described herein, continued to divide and reached the numbers of 1.000.000 at the passage 2, adherent culture day 11 and as much as 80.875.000 at passage 6. In contrast to our method, the cells in the adherent culture cultivated according to the Dieckmann et al. (loc. cit.) protocol reached 710.000 cells at passage 1 of the adherent culture, as the highest cell number and 650.000 cells by passage 2 at day 11 of the adherent culture. Unlike the cells cultivated upon the method described herein, the cells cultivated according to the Dieckmann (loc. cit.) method decreased in numbers with further passages (FIG. 15,16).

Genetycine Treatment

Figure 15:
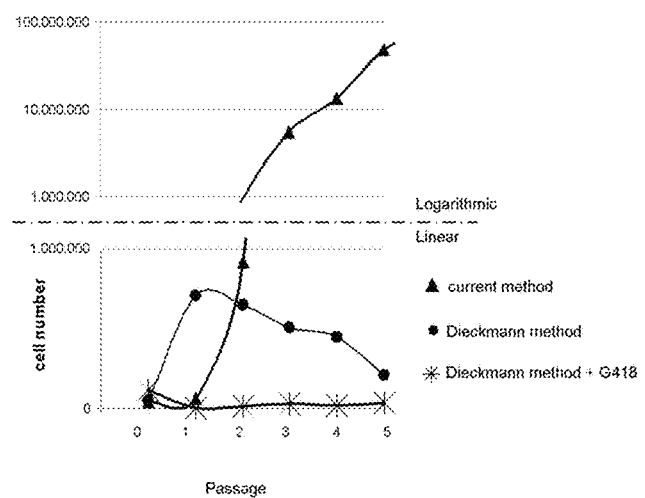
FIG. 15 is a graphical representation of the comparative cell growth in the adherent culture growth curves of ORS cells cultivated according to: (▲) the current method, (●) Dieckmann method, and (*) Dieckmann method with Geneticin supplement during the first 6 passages of adherent culture.

Additional treatment of adherent culture by Dieckmann (loc. cit.) with 50 µg/ml Geneticin with as a corresponding selection measure used in our current method resulted with extremely low numbers of survivor cells (<2% confluence) (FIG. 15,16).

The cells cultivated according to the current method reached higher numbers than the cells cultivated according to Dieckmann method (loc. cit.).

Conclusions

ORS Surface Changes

Collagenase effect on loosening the extracellular matrix through collagen proteolysis had obviously enabled easier migration of the cells out of ORS. This effect is visible by the enlarged surface of the ORS and by a more intensive migration of cells from ORS to the nylon mesh (FIG. 14). The initial growth of ORS in follicles digested with Collagenase V as per the current method exceeded that of non-digested follicles according to the Dieckmann (loc. cit.) method on all the days of adherent culture following day 0. That gave the method according to the invention the advantage of harvesting more cells from the medium-air-interface follicle culture and having more cells for the set-up of the adherent culture to start with. The number of cells harvested from the follicles cultivated by the current method on day 0 of the adherent culture exceeded that of Dieckmann (loc. cit.) method by factor 1.84 (FIG. 15).

Comparative Growth in the Adherent Culture

The cells in the adherent culture were continuously dividing in cultivation experiments according to the method described herein, reaching 1.000.000 cells at the passage 2 of the adherent culture, (half the time needed for the same number by Dieckmann et al. (loc. cit.)) and as much as 80.875.000 by the passage 6. The cells cultivated according to the Dieckmann (loc. cit.) method never reached those numbers, as a matter of fact, their numbers persistently declined after the passage 2 of the adherent culture.

Genetycine Treatment

Clearly, the portion of fibroblasts and keratinocytes in the material harvested from medium-air-interface follicle culture was much higher in the preparation according to the Dieckmann (loc. cit.) method, since most of them died during the Geneticin selection and an extremely low number of cells survived the Geneticin treatment, indicating that the Dieckmann (loc. cit.) method could not provide enough stem cells and precursors to quickly cultivate melanocytes in the adherent culture (FIG. 15). In contrast to the outcome of Geneticin selection of the cells cultivated according to Dieckmann et al. (loc. cit.), large number of cells cultivated as described herein survived this selection step and were able to give raise to very high cell numbers (FIG. 15).

Synergy of the higher start number of stem cells and precursors and more favourable adherent culture conditions given by the current method significantly advanced the yield of HM (FIG. 15).

Example 3

The Melanocytes Obtainable by the Herein Provided Method are Distinct from Known Melanocytes Even though melanocytes obtained according to the present invention (HM) correspond morphologically and functionally to adult skin melanocytes, they are a distinct and novel cell entity, as shown by the expression of cell surface markers (Tables 1-5) and by quantitative morphological parameters (FIG. 17).

Material and Methods

Morphological Characteristics

Surface of cells and dendrite length were measured by the means of Nikon NIS Elements BR (Version: 3.00) software. Total of 5 cells per experiment in 3 cultivation experiments, as described in the example 1, were evaluated. The surface of the cells was selected by the means of an adjustable polygonal frame and the surface values were read out by the software. The dendrite length was measured by a multipoint line length measuring tool.

Surface Marker Analysis by Lyoplate, FACS Measurements

Expression of surface markers was analysed by the means of BD Lyoplate Human Cell Surface Marker Screening Panel. This panel of 242 antibodies against human cell surface markers was used to label Normal Human Epidermal Melanocytes (NHEM) and ORS-derived melanocytes (HM). The cells were cultivated and characterized as described in the methods section of the Example 1, harvested in passages 10 to 11 and resuspended in Stain Buffer provided by the manufacturer. Aliquots of 200.000 cells/well were seeded in 96-well plates. Cells in each well were labelled with a separate mouse-generated or rat-generated primary antibody for a single surface marker and subsequently labelled with a corresponding secondary antibody against mouse or rat, respectively, labelled with Alexa 647 fluorophore. Between the 40-minute incubation steps, the cells were washed with Stain Buffer and centrifuged at 300 g for 4 minutes. After the staining, labelled cells were fixed for 10 minutes with 4% paraformaldehyde, washed and measured by the means of Becton Dickinson FACS Array system. The measurements were analysed using BD DIVA Software. Negative controls (unlabelled cells) were used to establish the threshold of the fluorescence signal. Fluorescence intensity of $2 \times 10^3$ was set as a threshold of marker expression Fluorescence intensity above the threshold in at least one proband was marked as positive expression (+).

Results

Morphological Characteristics

NHEM cells display an average surface of $377 \pm 135$ µm$^2$, whereas the HM display $290 \pm 74$ µm$^2$; hereby, NHEM soma is 23% larger in surface than HM soma (p=0.0451). Dendrites of NHEM are in average $35.73 \pm 15$ µm long, which is 39% longer than the $21.57 \pm 10$ µm long dendrites of the HM cells (p=0.045). NHEM have a slightly higher average number of dendrites ($3.13 \pm 1.19$) than HM ($2.47 \pm 0.64$), (p=0.065, non-significant) (FIG. 17).

Surface Markers

Out of 242 examined cell surface markers, 229 were expressed in HM, out of which 13 markers exclusively in HM (5.37% of the total number of cell markers). 229 markers were expressed in NHEM, 13 markers exclusively in NHEM (5.37%). Both NHEM and HM expressed 84 cell surface markers out of 242 of all examined markers. Differences in the cell surface marker expression between NHEM and HM comprise 10.74% of all examined markers and 34.7% of the expressed markers (Table 1-5).

Most of the markers that are differentially expressed between HM and NHEM are involved in regulation of immunity (CD195 CD108 CD40 CD36 CD15s CD282 CD173, CD274 in HM, CD1, CD28, CD79b, CD137, CD282, HLA-A2(A2), HLA-DQ in NHEM) and do not play a major role in development. Certain markers are generally functional or expressed in other lineages than melanocytic (CD40a, CD40b receptors for mesenchymal cell mitogens in HM, neuronally expressed adhesion molecule CD57 in NHEM). Markers normally expressed in melanocytes, CD117 and CD221, were expressed in NHEM and not in HM.

Tables 2 and 3 show surface markers that are differentially expressed in NHEM cells and melanocytes obtainable by the herein provided method (HM). Tables 4 and 5 show a comprehensive list of surface markers expressed in NHEM cells and melanocytes obtainable by the herein provided method (HM).

The markers characteristic for NHEM and HM respectively, have been assigned a NP number from the NCBI protein database (www.ncbi.nlm.nih.gov/protein). The use of such protein databases are known and therefore the corresponding amino acid and nucleic acid sequences of the markers to be used herein are easily accessible to a person skilled in the art.

Conclusions

Morphological Parameters

HM and NHEM share a common morphology, both have a large soma with protruded dendrites. HM display a smaller cell surface, shorter dendrites in a somewhat lower number than HM.

Surface Markers

The melanocytes obtained in accordance with the present invention and NHEM differ in surface marker expression (10.74% of the 242 examined markers) and overall marker expression (34.7% of all expressed markers). The difference in marker expression reflects a difference in cellular identity between HM and NHEM.

Expression of markers typical for other lineages complies with the nature of HM and NHEM. Expression of CD57, neuronal adhesion molecule, goes along with the common developmental origin of melanocytes and neural cells. CD40a, CD40b are receptors for mitogens in mesenchymal cells, which might render HM as susceptible to mesenchymal signalling cues; nevertheless, it is not within goals of this application to place HM in mesenchymal niche.

CD40a, CD40b, CD104 and CD106 are involved cell growth and adhesion and expressed in HM. Along with the absence CD117 expression, this reflects the stem cell origin of HM and points towards residual naivity of the HM cells, placing them in advanced partially melanotic melanoblast stage, the last before the full adult melanotic melanocyte stage.

CD221 (Insulin-like Growth Factor 1 tyrosine kinase receptor) is expressed in most human cells. CD221 mediates Insulin-like growth factor IGF-1 and IGF-2 signalling that affects cell growth, a very important feature for the cell culture. Absence of CD221 expression in HM deprives the HM cells from IGF-1 and IGF-2 signalling through this receptor and renders the IGF-1 and IGF-2 factors to a competitive binding of Insulin receptors. This does not interfere with our cultivation system, since the insulin supplement in the medium eliminates this competitive binding with its 100-fold higher affinity to insulin receptors and allows normal cell growth.

The melanocytes obtained herein differ in expressed markers and in qualitative morphologic traits which can be quantified as described herein above. Due to these differences, the herein provided and obtained melanocytes are a novel cellular entity Series of similarities at different levels of characterization show that ORS-differentiated HM are morphologically and functionally a peer to the epidermal skin-derived NHEM. Those features qualitatively and quantitatively show that the HM are a good substitute for NHEM, which means a great deal given that they are obtained non-invasively.

ORS melanocytes express the same intracellular markers (Tyrosinase, gp100 variants), sustain an active enzymatic set for melanogenesis (Tyrosinase, TRP-1 And TRP-2) that converts L-DOPA substrate into melanin, displaying ability to produce melanin from the supplemented substrate as well as spontaneously. Moreover, HM are able to migrate and populate novel niches. As we have shown, the HM are morphologically quite similar to the NHEM, apart from smaller soma and shorter dendrites, as determined by Forward Scatter in FACS analysis as well as by quantitative morphological parameters such as cell surface and dendrite length. Also, the cell surface marker expression differs between NHEM and HM. Due to these differences the herein provided melanocytes (HM) are a new cellular entity compared to epidermal NHEM. Accordingly, the melanocytes obtainable by the herein provided method are novel.

TABLE 1

Table of differences between epidermal melanocytes (NHEM) and ORS-derived melanocytes (HM) obtained in accordance with the present invention in surface marker expression.

| | complete difference in expression | | | partial difference in expression | | |
|---|---|---|---|---|---|---|
| | % of markers | | | | | |
| | 10.74 | | | 7.44 | | |
| | not expressed in NHEM | not expressed in HM | stronger expression in NHEM | stronger expression in HM | expression varies between HM-NHEM and HM-HM | expression varies between HM probands |
| | % of markers | | | | | |
| | 5.37 | 5.37 | 1.24 | 0.83 | 3.72 | 1.65 |
| Nomenclature | CD1a | CD15s | CD49a | CD10 | CD27 | CD66 (a, c, d, e) |
| | CD28 | CD36 | CD49d | CD13 | CD90 | CD209 |
| | CD77 | CD40 | Disialoganglioside GD2 | | CD97 | CD271 |
| | CD79b | CD48 | | | CD99R | CD273 |
| | CD137 Ligand | CD57 | | | CD200 | |
| | CD140a | CD108 | | | CD337 | |
| | CD140b | CD112 | | | HLA-DR | |
| | CD282 | CD117 | | | HLA-DR, DP, DQ | |
| | HLA-A2 | CD163 | | | CD49f | |
| | HLA-DQ | CD195 | | | | |
| | CD104 | CD221 | | | | |
| | CD106 | CD274 | | | | |
| | CD142 | CD201 | | | | |

TABLE 2

Table of surface markers expressed in NHEM:

| Marker | Name | Reference |
|---|---|---|
| CD15s | sialyl Lewis X | Nat Chem Biol 2008; 4: 751 |
| CD36 | glycoprotein IV (gpIV) | NP_000063.2 |
| CD40 | TNF receptor superfamily member 5 | NP_001241.1 |
| CD48 | SLAMF2 | NP_001242959.1 |
| CD57 | HNK-1 (human natural killer-1) carbohydrate | NP_061114.2 |
| CD108 | Semaphorin 7A | NP_001139501.1 |
| CD112 | Poliovirus receptor-related 2 (herpesvirus entry mediator B, nectin-2) | NP_001036189.1 |
| CD117 | c-kit ligand, mast/stem cell growth factor receptor Kit | NP_000213.1 |
| CD163 | scavenger receptor for the hemoglobin-haptoglobin complex | NP_004235.4 |
| CD195 | chemokine (C-C motif) receptor 5 | NP_000570.1 |
| CD221 | Insulin-like Growth Factor 1 (IGF-1) Receptor | NP_000866.1 |
| CD274 | Programmed cell death 1 ligand 1 | NP_001254635.1 |
| CD201 | primary receptor for protein C activation | NP_006395.2 |

TABLE 3

Table of surface markers expressed in melanocytes obtainable by the present method (also referred to herein as "HM")

| Marker | Name | Reference |
|---|---|---|
| CD1a | T-cell surface glycoprotein CD1a | NP_001754.2 |
| CD28 | Cluster of Differentiation 28 | NP_001230006.1 |
| CD77 | Ganglioside GA3 | NLM Registry Number 71965-57-6 |
| CD79b | immunoglobulin-associated beta | NP_000617.1 |
| CD137 Ligand | a) TNFRSF9 tumor necrosis factor receptor superfamily, member 9 | NP_001552.2 |
| CD140a | Alpha-type platelet-derived growth factor receptor | NP_006197.1 |
| CD140b | platelet-derived growth factor receptor, beta polypeptide PDGFRB | NP_002600.1 |
| CD282 | Toll-like receptor 2 | NP_003255.2 |
| HLA-A2 | human leukocyte antigen serotype within HLA-A "A" serotype group | NP_001229687. GenBank: AAA76608.2 GI:33187148 |
| HLA-DQ | human leukocyte antigen-DQ | NP_001230890.1, NP_002113.2 |
| CD104 | integrin beta-4 | NP_000204.3 |
| CD106 | vascular cell adhesion molecule 1 (VCAM-1) | NP_001069.1 |
| CD142 | platelet tissue factor, factor III, thrombokinase | NP_001171567.1 |

TABLE 4

Markers characteristic for NHEM melanocytes.

| | NHEM | Name | Reference |
|---|---|---|---|
| CD15s | + | sialyl Lewis X | Nat Chem Biol 2008; 4: 751 |
| CD36 | + | glycoprotein IV (gpIV) | NP_000063.2 |
| CD40 | + | TNF receptor superfamily member 5 | NP_001241.1 |
| CD48 | + | SLAMF2 | NP_001242959.1 |
| CD57 | + | HNK-1 (human natural killer-1) carbohydrate | NP_061114.2 |
| CD108 | + | Semaphorin 7A | NP_001139501.1 |
| CD112 | + | Poliovirus receptor-related 2 (herpesvirus entry mediator B, nectin-2) | NP_001036189.1 |

TABLE 4-continued

Markers characteristic for NHEM melanocytes.

| | NHEM | Name | Reference |
|---|---|---|---|
| CD117 | + | c-kit ligand, mast/stem cell growth factor receptor Kit | NP_000213.1 |
| CD163 | + | scavenger receptor for the hemoglobin-haptoglobin complex | NP_004235.4 |
| CD195 | + | chemokine (C-C motif) receptor 5 | NP_000570.1 |
| CD221 | + | Insulin-like Growth Factor 1 (IGF-1) Receptor | NP_000866.1 |
| CD274 | + | Programmed cell death 1 ligand 1 | NP_001254635.1 |
| CD201 | + | primary receptor for protein C activation | NP_006395.2 |
| CD9 | + | | |
| CD10 | + | | |
| CD13 | + | | |
| CD26 | + | | |
| CD27 | + | | |
| CD29 | + | | |
| CD34 | + | | |
| CD44 | + | | |
| CD45RB | + | | |
| CD45RO | + | | |
| CD46 | + | | |
| CD47 | + | | |
| CD49a | + | | |
| CD49b | + | | |
| CD49c | + | | |
| CD49d | + | | |
| CD49e | + | | |
| CD51/61 | + | | |
| CD54 | + | | |
| CD55 | + | | |
| CD56 | + | | |
| CD58 | + | | |
| CD59 | + | | |
| CD61 | + | | |
| CD63 | + | | |
| CD66 (a, c, d, e) | + | | |
| CD71 | + | | |
| CD73 | + | | |
| CD81 | + | | |
| CD90 | + | | |
| CD91 | + | | |
| CD95 | + | | |
| CD97 | + | | |
| CD98 | + | | |
| CD99 | + | | |
| CD99R | + | | |
| CD105 | + | | |
| CD107a | + | | |
| CD107b | + | | |
| CD109 | + | | |
| CD119 | + | | |
| CD120a | + | | |
| CD130 | + | | |
| CD141 | + | | |
| CD146 | + | | |
| CD147 | + | | |
| CD151 | + | | |
| CD152 | + | | |
| CD153 | + | | |
| CD164 | + | | |
| CD165 | + | | |
| CD166 | + | | |
| CD171 | + | | |
| CD183 | + | | |
| CD184 | + | | |
| CD196 | + | | |
| CD200 | + | | |
| CD209 | + | | |
| CD227 | + | | |
| CD271 | + | | |
| CD273 | + | | |
| CD321 (F11 Rcptr) | + | | |
| CD337 | + | | |
| CD340 (Her2) | + | | |
| β2micro | + | | |
| Hem. Prog. Cell | + | | |
| HLA-A, B, C | + | | |

TABLE 4-continued

Markers characteristic for NHEM melanocytes.

| | NHEM | Name | Reference |
|---|---|---|---|
| HLA-DR | + | | |
| HLA-DR, DP, DQ | + | | |
| Disialoganglioside GD2 | + | | |
| CD49f | + | | |
| CD1b | − | | |
| CD1d | − | | |
| CD2 | − | | |
| CD3 | − | | |
| CD4 | − | | |
| CD4v4 | − | | |
| CD5 | − | | |
| CD6 | − | | |
| CD7 | − | | |
| CD8a | − | | |
| CD8b | − | | |
| CD11a | − | | |
| CD11b | − | | |
| CD11c | − | | |
| CD14 | − | | |
| CD15 | − | | |
| CD16 | − | | |
| CD18 | − | | |
| CD19 | − | | |
| CD20 | − | | |
| CD21 | − | | |
| CD22 | − | | |
| CD23 | − | | |
| CD24 | − | | |
| CD25 | − | | |
| CD30 | − | | |
| CD31 | − | | |
| CD32 | − | | |
| CD33 | − | | |
| CD35 | − | | |
| CD37 | − | | |
| CD38 | − | | |
| CD39 | − | | |
| CD41a | − | | |
| CD41b | − | | |
| CD42a | − | | |
| CD42b | − | | |
| CD43 | − | | |
| CD45 | − | | |
| CD45RA | − | | |
| CD50 | − | | |
| CD53 | − | | |
| CD62E | − | | |
| CD62L | − | | |
| CD62P | − | | |
| CD64 | − | | |
| CD66b | − | | |
| CD66f | − | | |
| CD69 | − | | |
| CD70 | − | | |
| CD72 | − | | |
| CD74 | − | | |
| CD75 | − | | |
| CD80 | − | | |
| CD83 | − | | |
| CD84 | − | | |
| CD85 | − | | |
| CD86 | − | | |
| CD87 | − | | |
| CD88 | − | | |
| CD89 | − | | |
| CDw93 | − | | |
| CD94 | − | | |
| CD100 | − | | |
| CD102 | − | | |
| CD103 | − | | |
| CD114 | − | | |
| CD116 | − | | |
| CD118 (LIFR cptr) | − | | |

TABLE 4-continued

Markers characteristic for NHEM melanocytes.

| Name | NHEM | Reference |
|---|---|---|
| CD121a | − | |
| CD121b | − | |
| CD122 | − | |
| CD123 | − | |
| CD124 | − | |
| CD126 | − | |
| CD127 | − | |
| CD128b | − | |
| CD134 | − | |
| CD135 | − | |
| CD137 | − | |
| CD138 | − | |
| CD144 | − | |
| CD150 | − | |
| CD154 | − | |
| CD158a | − | |
| CD158b | − | |
| CD161 | − | |
| CD162 | − | |
| CD172b | − | |
| CD177 | − | |
| CD178 | − | |
| CD180 | − | |
| CD181 | − | |
| CD193 | − | |
| CD197 | − | |
| CD205 | − | |
| CD206 | − | |
| CD220 | − | |
| CD226 | − | |
| CD229 | − | |
| CD231 | − | |
| CD235a | − | |
| CD243 (p-glycoProtein) | − | |
| CD244 | − | |
| CD255 (Tweak) | − | |
| CD268 | − | |
| CD275 (B7-H2) | − | |
| CD278 | − | |
| Buffer | − | |
| CD279 | − | |
| CD305 (LAIR-1) | − | |
| CD309 | − | |
| CD314 (NKG2D) | − | |
| CDw327 | − | |
| CDw328 | − | |
| CDw329 | − | |
| CD335 (NKP46) | − | |
| CD336 | − | |
| CD338 (ABCG2) | − | |
| αβTCR | − | |
| BLTR-1 | − | |
| CLIP | − | |
| CMRF-44 | − | |
| CMRF-56 | − | |
| EGF Receptor | − | |
| fMLP Receptor | − | |
| γδTCR | − | |
| Invariant NKT | − | |
| MIC A/B | − | |
| NKB1 | − | |
| SSEA-1 | − | |
| SSEA-4 | − | |
| TRA-1-60 | − | |
| TRA-1-81 | − | |
| Vβ 23 | − | |
| Vβ 8 | − | |
| mIgM | − | |
| mIgG1 | − | |
| mIgG2a | − | |
| mIgG2b | − | |
| mIgG3 | − | |
| CD120b | − | |
| CD132 | − | |
| CD210 | − | |

TABLE 4-continued

Markers characteristic for NHEM melanocytes.

| | NHEM | Name | Reference |
|---|---|---|---|
| CD212 | − | | |
| CD267 | − | | |
| CD294 | − | | |
| CD326 | − | | |
| Cutaneous Lymph. Antigen | − | | |
| Integrin β7 | − | | |
| SSEA-3 | − | | |
| rIgM | − | | |
| rIgG1 | − | | |
| rIgG2a | − | | |
| rIgG2b | − | | |

TABLE 5

Markers characteristic for melanocytes obtainable by the method of the present invention (HM).

| | HM | Name | Reference |
|---|---|---|---|
| CD1a | + | T-cell surface glycoprotein CD1a | NP_001754.2 |
| CD28 | + | Cluster of Differentiation 28 | NP_001230006.1 |
| CD77 | + | Ganglioside GA3 | NLM Registry Number 71965-57-6 |
| CD79b | + | immunoglobulin-associated beta | NP_000617.1 |
| CD137 Ligand | + | a) TNFRSF9 tumor necrosis factor receptor superfamily, member 9 | NP_001552.2 |
| CD140a | + | Alpha-type platelet-derived growth factor receptor | NP_006197.1 |
| CD140b | + | platelet-derived growth factor receptor, beta polypeptide PDGFRB | NP_002600.1 |
| CD282 | + | Toll-like receptor 2 | NP_003255.2 |
| HLA-A2 | + | human leukocyte antigen serotype within HLA-A "A" serotype group | NP_001229687.1 GenBank: AAA76608.2 GI:33187148 |
| HLA-DQ | + | human leukocyte antigen-DQ | NP_001230890.1, NP_002113.2 |
| CD104 | + | integrin beta-4 | NP_000204.3 |
| CD106 | + | vascular cell adhesion molecule 1 (VCAM-1) | NP_001069.1 |
| CD142 | + | platelet tissue factor, factor III, thrombokinase | NP_001171567.1 |
| CD9 | + | | |
| CD10 | + | | |
| CD13 | + | | |
| CD26 | + | | |
| CD27 | + | | |
| CD29 | + | | |
| CD34 | + | | |
| CD44 | + | | |
| CD45RB | + | | |
| CD45RO | + | | |
| CD46 | + | | |
| CD47 | + | | |
| CD49a | + | | |
| CD49b | + | | |
| CD49c | + | | |
| CD49d | + | | |
| CD49e | + | | |
| CD51/61 | + | | |
| CD54 | + | | |
| CD55 | + | | |
| CD56 | + | | |
| CD58 | + | | |
| CD59 | + | | |
| CD61 | + | | |
| CD63 | + | | |
| CD66 (a, c, d, e) | + | | |
| CD71 | + | | |
| CD73 | + | | |
| CD81 | + | | |
| CD90 | + | | |
| CD91 | + | | |

TABLE 5-continued

Markers characteristic for melanocytes obtainable
by the method of the present invention (HM).

| | HM | Name | Reference |
|---|---|---|---|
| CD95 | + | | |
| CD97 | + | | |
| CD98 | + | | |
| CD99 | + | | |
| CD99R | + | | |
| CD105 | + | | |
| CD107a | + | | |
| CD107b | + | | |
| CD109 | + | | |
| CD119 | + | | |
| CD120a | + | | |
| CD130 | + | | |
| CD141 | + | | |
| CD146 | + | | |
| CD147 | + | | |
| CD151 | + | | |
| CD152 | + | | |
| CD153 | + | | |
| CD164 | + | | |
| CD165 | + | | |
| CD166 | + | | |
| CD171 | + | | |
| CD183 | + | | |
| CD184 | + | | |
| CD196 | + | | |
| CD200 | + | | |
| CD209 | + | | |
| CD227 | + | | |
| CD271 | + | | |
| CD273 | + | | |
| CD321 (F11 Rcptr) | + | | |
| CD337 | + | | |
| CD340 (Her2) | + | | |
| β2micro | + | | |
| Hem. Prog. Cell | + | | |
| HLA- A, B, C | + | | |
| HLA-DR | + | | |
| HLA- DR, DP, DQ | + | | |
| Disialoganglioside GD2 | + | | |
| CD49f | + | | |
| CD1b | − | | |
| CD1d | − | | |
| CD2 | − | | |
| CD3 | − | | |
| CD4 | − | | |
| CD4v4 | − | | |
| CD5 | − | | |
| CD6 | − | | |
| CD7 | − | | |
| CD8a | − | | |
| CD8b | − | | |
| CD11a | − | | |
| CD11b | − | | |
| CD11c | − | | |
| CD14 | − | | |
| CD15 | − | | |
| CD16 | − | | |
| CD18 | − | | |
| CD19 | − | | |
| CD20 | − | | |
| CD21 | − | | |
| CD22 | − | | |
| CD23 | − | | |
| CD24 | − | | |
| CD25 | − | | |
| CD30 | − | | |
| CD31 | − | | |
| CD32 | − | | |
| CD33 | − | | |
| CD35 | − | | |
| CD37 | − | | |
| CD38 | − | | |

TABLE 5-continued

Markers characteristic for melanocytes obtainable by the method of the present invention (HM).

| | HM | Name | Reference |
|---|---|---|---|
| CD39 | − | | |
| CD41a | − | | |
| CD41b | − | | |
| CD42a | − | | |
| CD42b | − | | |
| CD43 | − | | |
| CD45 | − | | |
| CD45RA | − | | |
| CD50 | − | | |
| CD53 | − | | |
| CD62E | − | | |
| CD62L | − | | |
| CD62P | − | | |
| CD64 | − | | |
| CD66b | − | | |
| CD66f | − | | |
| CD69 | − | | |
| CD70 | − | | |
| CD72 | − | | |
| CD74 | − | | |
| CD75 | − | | |
| CD80 | − | | |
| CD83 | − | | |
| CD84 | − | | |
| CD85 | − | | |
| CD86 | − | | |
| CD87 | − | | |
| CD88 | − | | |
| CD89 | − | | |
| CDw93 | − | | |
| CD94 | − | | |
| CD100 | − | | |
| CD102 | − | | |
| CD103 | − | | |
| CD114 | − | | |
| CD116 | − | | |
| CD118 (LIFR cptr) | − | | |
| CD121a | − | | |
| CD121b | − | | |
| CD122 | − | | |
| CD123 | − | | |
| CD124 | − | | |
| CD126 | − | | |
| CD127 | − | | |
| CD128b | − | | |
| CD134 | − | | |
| CD135 | − | | |
| CD137 | − | | |
| CD138 | − | | |
| CD144 | − | | |
| CD150 | − | | |
| CD154 | − | | |
| CD158a | − | | |
| CD158b | − | | |
| CD161 | − | | |
| CD162 | − | | |
| CD172b | − | | |
| CD177 | − | | |
| CD178 | − | | |
| CD180 | − | | |
| CD181 | − | | |
| CD193 | − | | |
| CD197 | − | | |
| CD205 | − | | |
| CD206 | − | | |
| CD220 | − | | |
| CD226 | − | | |
| CD229 | − | | |
| CD231 | − | | |
| CD235a | − | | |
| CD243 (p-glycoProtein) | − | | |
| CD244 | − | | |
| CD255 (Tweak) | − | | |

TABLE 5-continued

Markers characteristic for melanocytes obtainable by the method of the present invention (HM).

| | HM | Name | Reference |
|---|---|---|---|
| CD268 | − | | |
| CD275 (B7-H2) | − | | |
| CD278 | − | | |
| Buffer | − | | |
| CD279 | − | | |
| CD305 (LAIR-1) | − | | |
| CD309 | − | | |
| CD314 (NKG2D) | − | | |
| CDw327 | − | | |
| CDw328 | − | | |
| CDw329 | − | | |
| CD335 (NKP46) | − | | |
| CD336 | − | | |
| CD338 (ABCG2) | − | | |
| αβTCR | − | | |
| BLTR-1 | − | | |
| CLIP | − | | |
| CMRF-44 | − | | |
| CMRF-56 | − | | |
| EGF Receptor | − | | |
| fMLP Receptor | − | | |
| γδTCR | − | | |
| Invariant NKT | − | | |
| MIC A/B | − | | |
| NKB1 | − | | |
| SSEA-1 | − | | |
| SSEA-4 | − | | |
| TRA-1-60 | − | | |
| TRA-1-81 | − | | |
| Vβ 23 | − | | |
| Vβ 8 | − | | |
| mIgM | − | | |
| mIgG1 | − | | |
| mIgG2a | − | | |
| mIgG2b | − | | |
| mIgG3 | − | | |
| CD120b | − | | |
| CD132 | − | | |
| CD210 | − | | |
| CD212 | − | | |
| CD267 | − | | |
| CD294 | − | | |
| CD326 | − | | |
| Cutaneous Lymph. Antigen | − | | |
| Integrin β7 | − | | |
| SSEA-3 | − | | |
| rIgM | − | | |
| rIgG1 | − | | |
| rIgG2a | − | | |
| rIgG2b | − | | |

FIG. 1: Cultivation, selection and expansion of ORS cells from the ORS of the hair root into a pure culture of melanocytes within four weeks. A: Mid part of the epilated, prepared temporal hair root set on the Transwell microporous membrane (medium-air-interface) on the first day of cultivation. The compact Outer Root Sheath (ORS) is visible. B: Outgrown ORS with first cells migrating out of ORS. C: Multiplied cells are forming aggregations apart from the ORS. D: Pure culture of ORS melanocytes after four weeks of cultivation. The cells display a large soma and triple to multiple dendrites (tripolar to stellar morphology).

FIG. 2: Combination of methodological improvements in developing a pure culture of ORS melanocytes. A: Unprepared, untreated hair. ORS is compact (arrow) B: Unprepared, Collagenase V-treated hair with visible migrated cells outside ORS at mid-part and also outside the proximal (bulb) part (arrows). C: Prepared hair with the bulb part cut off (dash-line), untreated with Collagenase V, showing compact ORS (arrow). D: Prepared hair with the bulb part cut off (dash-line), treated with Collagenase V, showing outgrown ORS with migrated cells outside of ORS (arrow). Scale bars correspond to 500 μm. E: Outgrown, nearly confluent propagated cells outside of ORS on day 14 of culture. F: Primary culture of ORS cell pool developed from non-collagenised hairs on day 20. Several cell types can be seen. G: Primary culture of ORS cell pool developed from collagenised hairs on day 20. The cultivated cells display a more typical morphology. H: pure culture of selected melanocytes on day 26. I: Differentiated melanocytes in the pure culture at day 30. Scale bars correspond to 100 nm.

FIG. 3: Immunocytochemical characterization of the ORS culture. A: NKI\beteb is expressed in all epidermal melanocytes (NHEM); B: Tyrosinase is expressed in all epidermal melanocytes (NHEM); C: CD 90 is expressed in all non-melanocyte cells, prevalently fibroblasts; D: NKI\beteb is expressed in almost all ORS melanocytes (HM); E: Tyrosinase is expressed in almost all HM; F: absence of CD 90 expression in pure HM-culture. Bars correspond to 50 µm.

FIG. 4: Purity of the ORS melanocyte culture. The grey bars are showing the percentage of NKI/beteb-positive melanocytes in culture. The table displays the procedures of expansion, differentiation and selection in culture, showing a clear trend of an increase of melanocytes in culture that reaches 96% of NKI-beteb-expressing melanocytes with proper combination of the cultivating procedures. Coll+/− corresponds to Collagenase V treatment, HW+ stands for presence of the bulb, HW− stands for absence of the bulb (The bulb has been severed from the rest of the follicle), G+/− stands for Geneticin treatment, DLM for DermaLife culture media applied. The black bar represents epidermal melanocyte control (differentiated NHEM), grown in a separate culture, showing 99% of NKI/beteb-expressing cells. All of the differences are statistically significant ($p<0.05$ to very highly significant ($p<0.005$), except the differences between DLM/−Col/−HW/+G (non-digested shortened follicles treated with Geneticin and differentiated in DLM medium) and the rest of the categories.

FIG. 5: Fibroblast contamination in the ORS melanocyte culture. The grey bars are showing the percentage of CD-90-positive cells in culture (prevalently fibroblasts). The table displays the procedures of expansion, differentiation and selection of melanocytes in culture, showing a clear trend of a decrease of fibroblasts in culture that reaches 2% of CD-90-expressing cells with the optimal combination of the procedures. Coll+/− corresponds to Collagenase V treatment, HW+ stands for presence of the bulb, HW− stands for absence of the bulb (The bulb has been severed from the rest of the root), G+/− stands for Geneticin treatment, DLM for DermaLife culture media applied. The white bar represents fibroblast control, grown in a separate culture, showing 100% of CD-90-expressing cells. All of the differences are statistically significant ($p<0.05$) to very highly significant ($p<0.005$), except the differences between DLM/−Col/−HW/+G and the rest of the categories.

Figure 6:
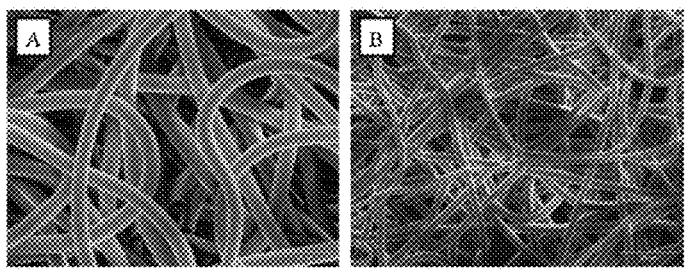
FIGS. 6A-6B represent exemplary images of a Policaprolactone (PCL) scaffold structure. A: REM capture of the 8 to 10 μm fibre. B: REM capture of the 2-3 μm fibre.

FIG. 6: Policaprolactone (PCL) scaffold structure. A: REM capture of the 8 to 10 µm fibre, 800-fold magnification. B: REM capture of the 2-3 µm fibre, 800 fold magnification. The scale bars correspond to 25 µm.

FIG. 7: Laser-Scanning Microscope capture of HM and NHEM on PCL Scaffolds. PCL-fibre (signal from reflected red light). NHEM melanocytes expressing Tyrosinase (green fluorescence) and the nuclei (DAPI UV-fluorescence) are visible. A: HM expressing Tyrosinase; B: NHEM expressing NKI\beteb; C: Side view (cross-section 3-D model) of the ORS melanocyte-populated PCL-Scaffold; HM have been labelled with Tyrosinase antibody (green signal). D: Side view (cross-section 3-D model) of the epidermal melanocyte-populated PCL-Scaffold.

The cross-sections show that the cells are populating the full depth of PCL scaffold. Scale bars correspond to 200 nm. The arrows are pointing at typical cell soma and extended dendrites interfaced with mesh fibre.

FIG. 8: Melanocyte marker expression on PCL scaffolds and on polystyrene adherent surface. The ratio of the number of nuclei against marker-positive cells is expressed as percentage. The Tyrosinase and NKI/beteb marker expression of epidermal (dark brown) and ORS melanocytes (beige) is equal to that of epidermal melanocytes on polystyrene adherent surface (black), showing that both HM and NHEM are maintaining their features on the PCL scaffolds.

FIG. 9: Both epidermal melanocytes (NHEM) and ORS melanocytes (HM) are forming melanosomes which are ready to be secreted from the end of the dendrites. The figure shows NKI/beteb labelling of melanosomes in NHEM and HM.

A: NHEMs on 3 µm PCL scaffold, B: NHEMs on 10 µm PCL scaffold C: HM on 3 µm PCL scaffold D: HM on 10 µm PCL scaffold. The scale bars correspond to 50 µm, at 40-fold magnification.

FIG. 10: Melanin content and L-DOPA-tautomerase activity of NHEM and HM on PCL scaffolds and adherent surfaces. All graphs are displaying clear trend of higher melanin production and L-DOPA-tautomerase activity on PCL scaffolds than at PS-adherent surfaces. Black bars represent the NHEM and grey bars the HM. (A) Melanin content in epidermal melanocytes on PCL scaffolds compared to adherent surface: Epidermal melanocytes produce 4.59 more melanin on PCL scaffolds than on the adherent polystyrene surfaces. (B) Melanin content in ORS melanocytes on PCL scaffolds compared to adherent surface: HM ORS melanocytes produce 2.58-fold more melanin on PCL scaffolds than on the adherent polystyrene surfaces. (C) L-DOPA activity in epidermal melanocytes on PCL scaffolds compared to adherent surface: Epidermal melanocytes convert 6.65-fold more L-DOPA on the PCL scaffolds than on the adherent polystyrene surfaces. (D) L-DOPA activity in ORS melanocytes on PCL scaffolds compared to adherent surface: HM ORS melanocytes convert 1.72-fold more L-DOPA on PCL scaffolds than on the adherent polystyrene surfaces. All values are shown relative to the corresponding values of a particular cell type on adherent surface, which are taken as 100%. All of the differences are highly statistically significant ($p<0.01$ to very highly significant ($p<0.005$).

FIG. 11: Outer root sheath melanocytes (HM ORS) embedded in the keratinocyte epidermal equivalent remain in the lower layer of the graft, equivalent to epidermal stratum basale, and express melanocyte markers. Tyrosinase and nuclear DAPI signals are visible. A: Epidermal melanocytes, normal light; B: Epidermal melanocytes, fluorescence.

Scale bar corresponds to 200 µm.

FIG. 12: Immunocytochemical characterization of the controls: expression of NKI-beteb in normal human epidermal melanocytes (NHEM) (a), Tyrosinase in epidermal melanocytes (b), CD-90 expression in pure dermal fibroblast culture (c), lack of CD-90 expression in HM culture (d), HM in culture without L-DOPA addition (e), IBMX-mediated changes in HM morphology and increased melanin content, without L-DOPA (f), melanin content upon L-DOPA substrate addition in HM (g) and increase in melanin content upon L-DOPA addition in IBMX-pre-treated HM (h). Scale bars (a-d) correspond to 50 µM, bars (e-f) to 100 µm.

FIG. 13.

Comparative changes of the Outer Root Sheath surface

Both the current method (♦) and the method of Dieckmann et al. (loc. cit.) (■) comprised an increase of the ORS surface. The surface increase is significantly higher in ORS of the follicles cultivated according to the current protocol in comparison with that of the Dieckmann method (loc. cit.), as measured at day 7 and day 14.

FIG. 14. Graphic display of comparative ORS surface changes.

(a) current method, day 0 (b) Dieckmann method (loc. cit.), day 0 (c) current method, day 7 (d) Dieckmann method (loc. cit.), day 7 (e) current method, day 14 (f) Dieckmann method (loc. cit.), day 14.

The hair follicles cultivated in the medium-air-interface upon the current method (a,c,e) displayed higher increase in ORS surface than those cultivated according to the Dieckmann (loc. cit.) method (b,d,e). On day 0, the follicles are compact (a,b). On day 7, outgrowth and migration of the cells was evident (c,d), as well as on day 14 (e,f). Stronger outgrowth of the follicles cultivated according to the current method is visible.

FIG. 15. Comparative cell growth in the adherent culture

Growth curves of ORS cells cultivated according to (▲) the current method, (●) Dieckmann (loc. cit.) method, (*) Dieckmann (loc. cit.) method with Geneticin supplement during the first 6 passages of adherent culture. The lower part of the graph is displayed linearity and the upper part logarithmically. The cells cultivated upon the method described herein reached the number of 1.000.000 cells by the second passage of adherent culture.

FIG. 16. Comparative growth in the adherent culture, per hair follicle.

Growth curves of ORS cells per sampled hair follicle cultivated according to (▲) the current method, (●) Dieckmann (loc. cit.) method, (*) Dieckmann (loc. cit.) method with Geneticin supplement during the first 6 passages of adherent culture. The graph is displayed logarithmically.

FIG. 17.

Different size of cell soma and dendrite length in NHEM and HM
(a) Relative cell size of NHEM and HM measured by Forward Scatter Plot (x-axis)
(b) Cell size of NHEM and HM in $\mu m^2$
(c) Dendrite length of NHEM and HM in $\mu m$

What is claimed is:

1. A method for generating melanocytes from outer root sheath cells comprising the steps of:
   (i) removing a bulb of an epilated human hair;
   (ii) incubating the epilated hair of step (i) with collagenase under conditions effective to separate outer root sheath cells from the outer root sheath, wherein the separation of the outer root sheath cells comprises migration of the outer root sheath cells from the outer root sheath, and wherein the outer root sheath cells include stem cells and precursor cells;
   (iii) cultivating the separated outer root sheath cells from step (ii) in a medium comprising one or more growth factors for differentiation into melanotic melanocytes; and
   (iv) differentiating the separated outer root sheath cells into melanotic melanocytes by the cultivation of step (iii).

2. The method according to claim 1, further comprising a step between step (ii) and (iii) of washing the epilated hair of step (i) with a washing solution after incubation with the collagenase.

3. The method according to claim 1, further comprising a step of: at least one of selecting or isolating the differenced melanotic melanocytes from the culture.

4. The method according to claim 3, wherein the melanocytes are isolated using at least one of anatomic selection of hair root subsections or differential trypsinization.

5. The method according to claim 3, wherein melanocytes are isolated using a Geneticin® treatment.

6. The method according to claim 3, wherein the isolation comprises isolating the melanocytes using differentiate trypsinization and subsequently Geneticin® treatment.

7. The method according to claim 1, wherein the collagenase is selected from the group consisting of collagenase I, collagenase IV and collagenase V.

8. The method according to claim 1, wherein the medium further comprises one or more compounds selected from the group consisting of β-adrenergic receptor ligands, epinephrine, $Ca^{2+}$, L-glutamine, insulin, fetal calf serum, human serum, and bovine pituitary gland extract.

9. The method according to claim 1, wherein the growth factors are selected from the group consisting of ethanolamine, phosphoethanolamine, hydrocortisone, basic fibroblast growth factor (bFGF), dibutyryl cyclic adenosine monophosphate (dbcAMP), melanocyte growth factor (MeGF), Kaposi's sarcoma derived FGF-like factor (hst/K-FGF), hepatocyte growth factor (HGF), stem cell growth factor (SCF), endothelin 1, alpha-melanocyte stimulating hormone (α-MSH), mixtures of native factors from medium conditioned by cultured human keratinocytes, bovine pituitary extract (BPE), bovine brain extract, and human serum.

10. The method according to claim 1, wherein the separation of the outer root sheath cells comprises migration of the outer root sheath cells from the outer root sheath to a mesh.

11. The method according to claim 10, wherein the mesh comprises a nylon mesh.

12. Melanotic melanocytes generated by the method according to claim 1.

13. A method for treating a disease or condition in a subject, comprising applying the melanocytes generated according to the method of claim 1 to a subject in need thereof, wherein the disease or condition is selected from the group consisting of: leukoderma, vitiligo, quadrichrome vitiligo, vitiligo ponctué, syndromic Albinism, Alezzandrini syndrome, Hermansky-Pudlak syndrome, Chédiak-Higashi syndrome, Griscelli syndrome, Elejalde syndrome, Griscelli syndrome type 2, Griscelli syndrome type 3, Waardenburg syndrome, Tietz syndrome, Cross-McKusick-Breen syndrome, ABCD syndrome, Albinism-deafness syndrome, Vogt-Koyanagi-Harada syndrome, oculocutaneous albinism, hypomelanosis, idiopathic guttate hypomelanosis, phylloid hypomelanosis, progressive macular hypomelanosis, piebaldism, nevus depigmentosus, postinflammatory hypopigmentation, pityriasis alba, Vagabond's leukomelanderma, Yemenite deaf-blind hypopigmentation syndrome, Wende-Bauckus syndrome, Woronoff's ring, amelanism, Leucism, diseases associated with depigmentation of the skin and conditions in need of repigmentation.

14. The method according to claim 13, wherein the melanocytes express at least one surface marker selected from the group consisting of: CD1a, CD28, CD77, CD79b, CD137 Ligand, CD140a, CD140b, CD282, HLA-A2, HLA-DQ, CD104, CD106, and CD142.

15. A method for producing a graft comprising melanocytes, said method comprising the steps of:
   (i) providing a suspension comprising melanocytes obtained by a method for generating melanocytes from stem cells according to claim 1;
   (ii) providing a biocompatible scaffold; and
   (iii) cultivating the melanocytes on said biocompatible scaffold.

16. The method according to claim 15, wherein the suspension of step (i) further comprises introducing keratinocytes.

17. The method according to claim 16, wherein the melanocytes are cultivated until the formation of a stratum basale.

18. The method according to claim 16, wherein the keratinocytes and melanocytes are provided in a ratio of 10:1.

19. The method according to claim 15, wherein the method further comprises the following steps:

(iv) stratifying keratinocytes on the melanocytes cultivated on the biocompatible scaffold;

(v) cultivating the keratinocytes and the melanocytes on the biocompatible scaffold.

20. The method according to claim 19, wherein the cultivation of keratinocytes over the melanocytes is performed in a medium-air interface until formation of a stratum corneum in step (iv).

21. The method according to claim 15, wherein the biocompatible scaffold comprises a three-dimensional fiber network.

22. The method according to claim 15, wherein the biocompatible scaffold comprises at least one of the materials selected from the group consisting of polycaprolactone (PCL), collagen, human collagen I, human collagen IV, human collagen V, fibrin, and gelatine.

23. A graft of melanocytes generated by the method according to claim 15.

24. A method for treating a disease in a subject, comprising applying the graft according to claim 23 to the subject, wherein the disease is selected from the group consisting of: leukoderma, vitiligo, quadrichrome vitiligo, vitiligo ponctué, syndromic Albinism, Alezzandrini syndrome, Hermansky-Pudlak syndrome, Chédiak-Higashi syndrome, Griscelli syndrome, Elejalde syndrome, Griscelli syndrome type 2, Griscelli syndrome type 3, Waardenburg syndrome, Tietz syndrome, Cross-McKusick-Breen syndrome, ABCD syndrome, Albinism-deafness syndrome, Vogt-Koyanagi-Harada syndrome, oculocutaneous albinism, hypomelanosis, idiopathic guttate hypomelanosis, phylloid hypomelanosis, progressive macular hypomelanosis, piebaldism, nevus depigmentosus, postinflammatory hypopigmentation, pityriasis alba, Vagabond's leukomelanderma, Yemenite deaf-blind hypopigmentation syndrome, Wende-Bauckus syndrome, Woronoff's ring, amelanism, Leucism, diseases associated with depigmentation of the skin, and conditions in need of repigmentation.

25. A graft comprising melanocytes obtained by the method according to claim 1 and a biocompatible scaffold.

26. The graft of claim 25, further comprising keratinocytes.

27. The graft of claim 26, wherein the keratinocytes are stratified on the melanocytes.

28. The graft of claim 26, wherein keratinocytes and melanocytes are provided in a ratio of 10:1.

29. The graft of claim 25, wherein the biocompatible scaffold comprises a three-dimensional fiber network.

30. The graft of claim 25, wherein the biocompatible scaffold comprises at least one material selected from the group comprising polycaprolactone (PCL), collagen, human collagen I, human collagen IV, human collagen V, fibrin, and gelatine.

* * * * *

UNITED STATES PATENT AND TRADEMARK OFFICE
CERTIFICATE OF CORRECTION

PATENT NO. : 9,801,977 B2  
APPLICATION NO. : 14/354545  
DATED : October 31, 2017  
INVENTOR(S) : Savkovic et al.

Page 1 of 5

It is certified that error appears in the above-identified patent and that said Letters Patent is hereby corrected as shown below:

On the Title Page

In Item (74), under "Attorney, Agent, or Firm", in Column 2, Line 2, delete "LLP." and insert -- LLP --.

On Page 2, in Item (56), under "OTHER PUBLICATIONS", in Column 2, Line 17, delete "1n" and insert -- in --.

On Page 2, in Item (56), under "OTHER PUBLICATIONS", in Column 2, Line 23, delete "1n" and insert -- in --.

In the Drawings

Replace Figs. 1A-D, Sheet 1 of 17, with the attached Sheet 1 of 17.

Replace Figs. 6A-B, Sheet 5 of 17, with the attached Sheet 5 of 17.

In the Specification

In Column 4, Line 12, delete "(iii) (ii)" and insert -- (ii) --.

In Column 4, Line 29, delete "Diekmann" and insert -- Dieckmann --.

In Column 7, Lines 37-38, delete "removing the bulb of an epilated human hair;" and insert -- i) removing the bulb of an epilated human hair; --, at Line 38, as a new subpoint.

In Column 7, Line 39, delete "i)" and insert -- ii) --.

In Column 7, Line 42, delete "ii)" and insert -- iii) --.

Signed and Sealed this  
Twentieth Day of February, 2018

Andrei Iancu  
*Director of the United States Patent and Trademark Office*

CERTIFICATE OF CORRECTION (continued)

U.S. Pat. No. 9,801,977 B2

In Column 7, Line 67, delete "osteocytic" and insert -- osteocytic) --.

In Column 8, Lines 28-29, delete "Cabenicilin, Thiostrepton," and insert -- Thiostrepton, --.

In Column 8, Line 41, delete "(0.25 μg/ml" and insert -- (0.25 pg/ml --.

In Column 8, Line 45, delete "-Carbenicillin," and insert -- Carbenicillin, --.

In Column 8, Line 46, delete "100 U/ml)" and insert -- 100 U/ml), --.

In Column 8, Line 54, delete "Spectinomycin)" and insert -- Spectinomycin --.

In Column 9, Line 53, delete "Dulbeccos" and insert -- Dulbecco's --.

In Column 13, Lines 18-19, delete "NGF-β 20 ng/ml)," and insert -- NGF-β (20 ng/ml), --.

In Column 13, Line 34, delete "NGF-β 20 ng/ml)," and insert -- NGF-β (20 ng/ml), --.

In Column 13, Line 65, delete "stem cell growth factor (SCF)," and insert -- stem cell factor (SCF), --.

In Column 14, Line 48, delete "Microphtalmia-associated Transcription Factor (MITF)" and insert -- Microphthalmia-associated Transcription Factor (MITF) --.

In Column 15, Lines 5-6, delete "melanocytes," and insert -- melanocytes; --.

In Column 16, Line 60, delete "(and up" and insert -- and up --.

In Column 17, Line 18, delete "HMB45." and insert -- HMB45). --.

In Column 18, Line 22, delete "one a marker" and insert -- one marker --.

In Column 18, Line 24, delete "analysed.'" and insert -- analyzed. --.

In Column 18, Line 65, delete "1990.)" and insert -- (1990.) --.

In Column 19, Line 62, delete "thereof)" and insert -- thereof). --.

In Column 22, Line 11, delete "basale The" and insert -- basale. The --.

In Column 24, Line 3, delete "(anatomically" and insert -- anatomically --.

In Column 26, Line 22, delete "(PBS," and insert -- (PBS), --.

In Column 26, Line 39, delete "10 Mm." and insert -- 10 min. --.

In Column 26, Lines 44-45, delete "(5 ng/ml)," and insert -- (5 μg/ml), --.

In Column 26, Line 45, delete "(50 ng/ml)," and insert -- (50 µg/ml), --.

In Column 26, Line 45, delete "(1 nM)," and insert -- (1 µM), --.

In Column 26, Line 46, delete "(50 ng/ml)," and insert -- (50 µg/ml), --.

In Column 27, Lines 31-32, delete "12-myristat 13-acetate (PMA, TPA)" and insert -- 12-myristate 13-acetate (PMA, TPA). --.

In Column 31, Line 22, delete "Mention," and insert -- invention, --.

In Column 34, Lines 27-28, delete "5 mg/ml," and insert -- 5 µg/ml, --.

In Column 34, Line 28, delete "0.5 mg/ml," and insert -- 0.5 µg/ml, --.

In Columns 39-40, in Table 3, under "Reference", Line 10, delete "NP_001229687." and insert -- NP_001229687.1 --.

In Column 54, Line 61, delete "100 nm." and insert -- 100 µm. --.

In Column 55, Line 18, delete "(p<0.05" and insert -- (p<0.05) --.

In Column 55, Line 55, delete "200 nm." and insert -- 200 µm. --.

In Column 56, Line 31, delete "(p<0.01" and insert -- (p<0.01) --.

In Column 56, Line 51, delete "50 µM," and insert -- 50 µm, --.

In Column 57, Line 12, delete "linearity" and insert -- linearily --.

In the Claims

In Column 58, Lines 10-11, in Claim 9, delete "stem cell growth factor (SCF)," and insert -- stem cell factor (SCF), --.

In Column 58, Lines 39-40, in Claim 13, delete "leukomelanderma," and insert -- leukomelanoderma, --.

In Column 59, Line 2, in Claim 19, delete "scaffold;" and insert -- scaffold; and --.

In Column 59, Line 16, in Claim 22, delete "gelatine" and insert -- gelatin --.

In Column 60, Line 6, in Claim 24, delete "leukomelanderma," and insert -- leukomelanoderma, --.

In Column 60, Line 25, in Claim 30, delete "gelatine" and insert -- gelatin --.

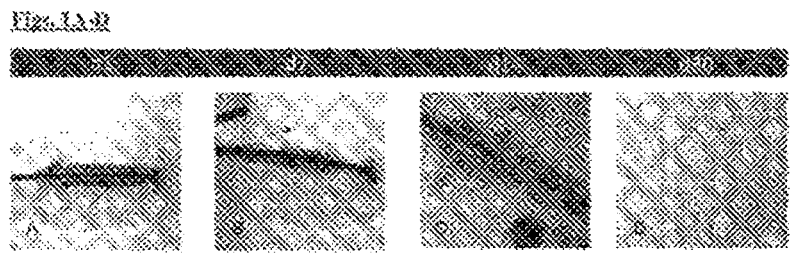

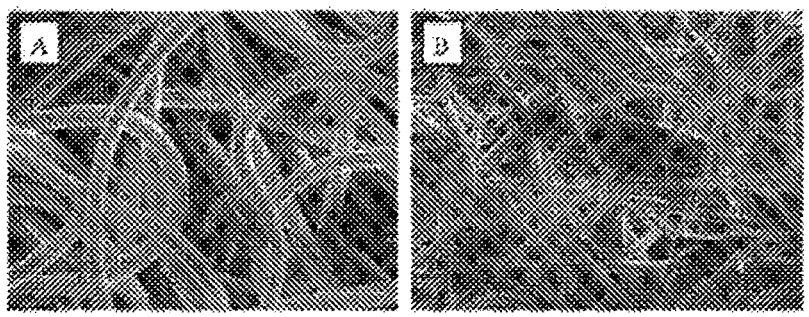
Figs. 6A-B